United States Patent [19]

Skuballa et al.

[11] Patent Number: 4,692,464
[45] Date of Patent: Sep. 8, 1987

[54] NOVEL PROSTACYCLIN DERIVATIVES AND A PROCESS FOR THE PREPARATION THEREOF

[75] Inventors: Werner Skuballa; Bernd Radüchel; Helmut Vorbrüggen; Gerda Mannesmann; Wolfgang Losert; Jorge Casals, all of Berlin, Fed. Rep. of Germany

[73] Assignee: Schering Aktiengesellschaft, Berlin and Berkgamen, Fed. Rep. of Germany

[21] Appl. No.: 352,411

[22] Filed: Feb. 26, 1982

Related U.S. Application Data

[62] Division of Ser. No. 86,506, Oct. 19, 1979, abandoned.

[30] Foreign Application Priority Data

Oct. 19, 1978 [DE] Fed. Rep. of Germany ....... 2845770

[51] Int. Cl.$^4$ ................. C07C 177/00; A61K 31/557
[52] U.S. Cl. .................................. 514/530; 514/573; 546/342; 548/562; 549/13; 549/17; 549/427; 549/501; 556/437; 560/56; 560/116; 560/119; 560/256; 562/466; 562/498; 562/501; 564/98
[58] Field of Search .............. 560/119, 116, 56, 256; 562/501, 466, 498; 564/98; 546/342; 549/13.7, 427, 501; 548/562; 556/437; 514/530, 573

[56] References Cited

U.S. PATENT DOCUMENTS 4,238,414  12/1980  Morton .............................. 564/453

FOREIGN PATENT DOCUMENTS 2013661  8/1979  United Kingdom ................ 560/119

OTHER PUBLICATIONS

March Advanced Org. Chem., 2nd Edition, p. 936 (1977).

*Primary Examiner*—Robert Gerstl
*Attorney, Agent, or Firm*—Millen & White

[57] ABSTRACT

Compounds of the formula

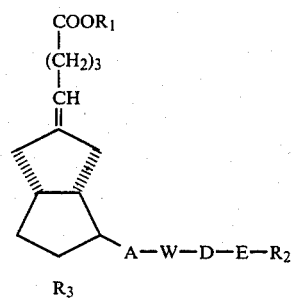

wherein
$R_1$ is (a) hydrogen, (b) $C_{1-10}$ alkyl, (c) $C_{1-10}$ alkyl substituted by halogen; $C_{1-4}$ alkoxy; $C_{6-10}$ aryl; $C_{6-10}$ aryl substituted by 1–3 halogen atoms, a phenyl group, 1–3 $C_{1-4}$ alkyl groups or a chloromethyl, fluoromethyl, trifluoromethyl, carboxy, hydroxy or $C_{1-4}$ alkoxy group; di-$C_{1-4}$-alkylamino; or tri-$C_{1-4}$-alkylammonium; (d) $C_{4-10}$ cycloalkyl, (e) $C_{4-10}$ cycloalkyl substituted by $C_{1-4}$ alkyl, (f) $C_{6-10}$ aryl, (g) $C_{6-10}$ aryl substituted by 1–3 halogen atoms, a phenyl group 1–3 $C_{1-4}$ alkyl groups or a chloromethyl, fluoromethyl, trifluoromethyl, carboxy, hydroxy or $C_{1-4}$ alkoxy group, or (h) an aromatic heterocycle of 5 or 6 ring atoms one of which is O, N or S;
A is —$CH_2$—$CH_2$—, trans—CH=CH— or —C≡C—;
W is hydroxymethylene, RO-methylene, $CH_3$ or $CH_3$,

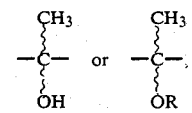

wherein OH or OR is in the α- or β-position and
R is an in vivo hydrolyzable and physiologically acceptable ether or acyl group which is conventional for modifying OH groups in prostaglandins;
D and E together are a direct bond, or
D is $C_{1-10}$ alkylene, $C_{1-10}$ alkenylene or $C_{1-10}$ alkynylene or one of these groups substituted by fluorine, and
E is oxygen, —C≡C— or a direct bond;
$R_2$ is (a) a $C_{1-10}$ hydrocarbon aliphatic radical, (b) a $C_{6-10}$ hydrocarbon aliphatic radical substituted by $C_{6-10}$ aryl or by $C_{6-10}$ aryl substituted by 1–3 halogen atoms, a phenyl group, 1–3 $C_{1-4}$ alkyl groups or a chloromethyl, fluoromethyl, trifluoromethyl, carboxy, hydroxy or $C_{1-4}$ alkoxy group; (c) $C_{4-10}$ cycloalkyl, (d) $C_{4-10}$ cycloalkyl substituted by $C_{1-4}$ alkyl, (e) $C_{6-10}$ aryl, (f) $C_{6-10}$ aryl substituted by 1–3 halogen atoms, a phenyl group, 1–3 $C_{1-4}$ alkyl groups or a chloromethyl, fluoromethyl, trifluoromethyl, carboxy, hydroxy or $C_{1-4}$ alkoxy group; or (h) an aromatic heterocycle of 5 or 6 ring atoms one of which is O, N or S; and
$R_3$ is OH or OR; and, when $R_1$ is hydrogen, the salts thereof with physiologically compatible bases, are effective as antihypertensive, bronchiodilators, thrombocyte aggregation inhibitors, inter alia.

31 Claims, No Drawings

NOVEL PROSTACYCLIN DERIVATIVES AND A PROCESS FOR THE PREPARATION THEREOF

This is a division of application Ser. No. 086,506 filed Oct. 19, 1979 abandoned.

BACKGROUND OF THE INVENTION

The present invention relates to novel prostacyclin derivatives, a process for the preparation thereof, as well as the use thereof as medicinal agents.

Prostacyclin ($PGI_2$), one of the primary factors in blood platelet aggregation, has a dilating effect on various blood vessels (Science 196:1072) and thus can be considered as an agent for lowering of blood pressure. $PGI_2$, however, does not possess the stability required for medicaments. For example, the half-life of $PGI_2$ at physiological pH values and at room temperature is merely a few minutes.

SUMMARY OF THE INVENTION

Accordingly, it is an object of this invention to provide prostacyclin derivatives which are highly stable, have a good duration of effectiveness and whose pharmacological activity is preserved.

Upon further study of the specification and appended claims, further objects and advantages of this invention will become apparent to those skilled in the art.

It has been found that replacement of the 9-ether oxygen atom in a prostacyclin by a methylene group stabilizes the prostacyclin; yet, the pharmacological spectrum of activity remains preserved and the duration of effectiveness is markedly prolonged.

Thus, the objects of this invention have been achieved by providing prostane derivatives of the Formula I

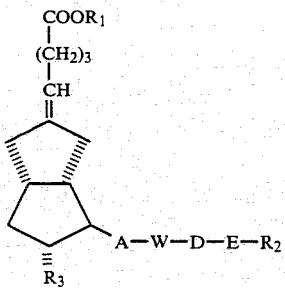

wherein
$R_1$ is hydrogen, alkyl, cycloalkyl, aryl or a heterocyclic residue;
A is $-CH_2-CH_2-$, trans$-CH=CH$ or $-C\equiv C-$;
W is free or functionally modified hydroxymethylene or free or functionally modified

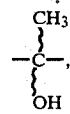

wherein OH is in the α- or β-position D and E together are a direct bond or
D is straight-chain or branched, saturated or unsaturated alkylene of 1-10 carbon atoms, optionally substituted by fluorine, and
E is oxygen, $-C\equiv C-$ or a direct bond;
$R_2$ is alkyl, cycloalkyl, optionally substituted aryl or a heterocyclic group; and
$R_3$ is free or functionally modified hydroxy; and, when $R_1$ is hydrogen, the salts thereof with physiologically compatible bases.

DETAILED DISCUSSION

Suitable alkyl groups $R_1$ include straight-chain or branched alkyl of 1–10 carbon atoms, such as, for example, methyl, ethyl, propyl, butyl, isobutyl, tert-butyl, pentyl, neopentyl, heptyl, hexyl, decyl and the like. Equivalent $R_1$ groups are such alkyl groups mono- to polysubstituted by halogen, $C_{1-4}$ alkoxy, optionally substituted $C_{6-10}$ aryl groups, di-$C_{1-4}$-alkylamines and tri-$C_{1-4}$-alkylammonium. Monosubstituted alkyl groups are preferred. Preferred alkyl groups $R_1$ are those of 1–4 carbon atoms, such as, for example, methyl, ethyl, propyl, dimethylaminopropyl, isobutyl and butyl.

Examples of such alkyl group substituents include fluorine, chlorine, or bromine, phenyl, dimethylamine, diethylamine, methoxy, ethoxy and the like. Suitable substituents for the aryl group substituents include those mentioned below in conjunction with the $R_1$ aryl groups, thereby forming substituted aryl groups equivalent to the mentioned aryl groups.

Suitable aryl groups $R_1$ include substituted as well as unsubstituted aryl groups, such as, for example, phenyl, 1-naphthyl, and 2-naphthyl, each of which can be substituted by 1–3 halogen atoms, a phenyl group, 1–3 $C_{1-4}$ alkyl groups or a chloromethyl, fluoromethyl, trifluoromethyl, carboxy, hydroxy or $C_{1-4}$ alkoxy group. Substitution in the 3- and 4-positions on the phenyl ring are preferred, for example, by fluorine, chlorine, alkoxy, or trifluoromethyl or in the 4-position by hydroxy.

The cycloalkyl group $R_1$ can contain 4–10, preferably 5 or 6 carbon atoms in the ring. The rigns can be substituted by alkyl groups of 1–4 carbon atoms. Examples include cyclopentyl, cyclohexyl, methylcyclohexyl and adamantyl.

Suitable heterocyclic groups $R_1$ include 5- and 6-membered aromatic heterocycles containing at least one hetero atom, preferably nitrogen, oxygen, or sulfur. Examples include 2-furyl, 2-thienyl, 2-pyridyl, 3-pyridyl, 4-pyridyl, oxazolyl, thiazolyl, pyrimidinyl, pyridazinyl, pyrazinyl, etc.

The hydroxy groups for $R_3$ and W can independently be functionally modified, for example, by etherification or esterification, wherein the free or modified hydroxy groups in W are in the α-position, free hydroxy groups being preferred. Suitable ether and acyl residues are fully conventional and well-known to persons skilled in the art, e.g., are in vivo hydrolyzable and physiologically acceptable ether or acyl groups which are conventional for modifying OH groups in prostacyclin type compounds. Preferred are readily cleavable ether residues, e.g., tetrahydropyranyl, tetrahydrofuranyl, α-ethoxyethyl, trimethylsilyl, dimethyl-tert-butylsilyl and tribenzylsilyl.

Suitable acyl residues include those of $C_{1-15}$ hydrocarbon carboxylic or sulfonic acids. Examples of such acyl residues include: acetyl, propionyl, butyryl, benzoyl, etc. In general, these conventional protective groups include, e.g., those disclosed in Mc. Omie. Ed., Protective Groups in Organic Chemistry, Plenum Press, N.Y., 1973, whose disclosure is incorporated by reference herein.

Suitable $R_2$ alkyl groups include straight-chain or branched, saturated or unsaturated aliphatic residues, preferably saturated residues of 1-10, especially 1-7 carbon atoms, which can optionally be substituted by $C_{6-10}$ aryl, which, in turn, can optionally be substituted, e.g., by those substituents mentioned above for the $R_1$ aryl groups. Examples include methyl, ethyl, propyl, butyl, isobutyl, tert-butyl, pentyl, hexyl, heptyl, octyl, butenyl, isobutenyl, propenyl, pentenyl, hexenyl, benzyl, p-chlorobenzyl, etc.

Suitable $R_2$ cycloalkyl groups include those of 4-10, preferably 5 and 6 carbon atoms in the ring. The rings can be substituted by alkyl groups of 1-4 carbon atoms. Examples include cyclopentyl, cyclohexyl, methylcyclohexyl and adamantyl.

Examples of substituted or unsubstituted aryl groups for $R_2$ include: phenyl, 1-naphthyl, and 2-naphthyl, each of which can be substituted by 1-3 halogen atoms, phenyl, 1-3 alkyl groups of 1-4 carbon atoms each or a chloromethyl, fluoromethyl, trifluoromethyl, carboxy, alkoxy or hydroxy group. Substitution in the 3- and 4-positions on the phenyl ring is preferred, for example, by fluorine, chlorine, alkoxy or trifluoromethyl, or in the 4-position by hydroxy.

Suitable heterocyclic groups $R_2$ include 5- and 6-membered aromatic heterocycles containing at least one hetero atom, preferably nitrogen, oxygen or sulfur. Examples include 2-furyl, 2-thienyl, 2-pyridyl, 3-pyridyl, 4-pyridyl, oxazolyl, thiazolyl, pyrimidinyl, pyridazinyl, pyrazinyl, etc.

Suitable as the aliphatic group D are straight-chain or branched-chain, saturated and unsaturated residues, preferably saturated ones of 1-10, especially 1-5 carbon atoms, which can optionally be substituted by 1—fluorine atoms. These include $C_{1-10}$ alkylene, $C_{1-10}$ alkenylene and $C_{1-10}$ alkynylene. Examples include methylene, fluoromethylene, ethylene, 1,2-propylene, ethylethylene, trimethylene, tetramethylene, pentamethylene, 1-methyltetramethylene, 1-methyltrimethylene, difluoromethylene, 1-fluoroethylene, 1,1-difluoromethylene, 1-methylene-ethylene and 1-methylene-tetramethylene.

Suitable bases for formation of salts of the free acids of Formula I ($R_1$=H) include inorganic and organic bases, which are fully conventional and well-known to those skilled in the art for the formation of physiologically compatible salts. Examples include: alkali hydroxides, such as sodium and potassium hydroxide, alkaline earth hydroxides, such as calcium hydroxide, ammonia, amines, such as ethanolamine, diethanolamine, triethanolamine, N-methylglucamine, morpholine and tris(hydroxymethyl)-methylamine, etc.

The invention relates furthermore to a process for the preparation of a prostane derivative of Formula I, comprising, in a conventional manner, reacting a compound of Formula II

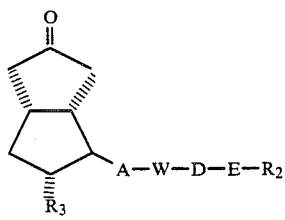

wherein $R_2$, $R_3$, A, W, D and E are as defined above, optionally after blocking any free hydroxy groups therein, with a Wittig reagent of Formula III

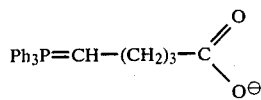

wherein Ph is phenyl. The reaction can be conducted conventionally unless otherwise indicated herein, e.g., as described in J. S. Bindra, *Prostaglandin Synthesis*, Page 210, Academic Press (N.Y.197 whose disclosure is incorporated by reference herein. Optionally, thereafter, in any desired sequence, any isomers can be separated, and/or blocked hydroxy groups can be liberated, and/or free hydroxy groups can be esterified or etherified, and/or free carboxy groups can be esterified, and/or esterified carboxy groups can be saponified and/or carboxy groups can be converted into a salt with a physiologically compatible base.

The reaction of a compound of Formula II with a Wittig reagent of Formula III, which can be produced by reacting the corresponding phosphonium salt with methanesulfinylmethyl sodium or methanesulfinylmethyl potassium or potassium tert-butylate in dimethyl sulfoxide, can be conducted at temperatures of 0°-100° C., preferably 20°-80° C., in an aprotic solvent, preferably dimethyl sulfoxide or dimethylformamide. The separation of the thus-obtained olefins of a Z- and E-configuration is conducted using fully conventional methods, for example, by column or layer chromatography.

The saponification of the prostaglandin esters is effected by following fully conventional methods known to those skilled in the art, for example, using alkaline catalysts. Similarly, the introduction of the ester group in the compounds wherein $R_1$ is $C_{1-10}$ alkyl is accomplished according to conventional methods known to persons skilled in the art. For example, the carboxy compounds can be reacted with diazo hydrocarbons in a conventional manner, for example, by mixing a solution of the diazo hydrocarbon in an inert solvent, preferably in diethyl ether, with the carboxy compound in the same or in another inert solvent, e.g., methylene chloride. After the reaction is terminated in 1-30 minutes, the solvent is removed and the ester is purified in conventional fashion. Diazoalkanes are either known or can be produced according to conventional methods [See, e.g., Org. Reactions, 8:389-394 (1954), whose disclosure is incorporated by reference herein].

The introduction of the ester group in the compounds wherein $R_1$ is a substituted or unsubstituted aryl group, can also be conducted according to methods known to persons skilled in the art. For example, the carboxy compounds can be reacted with the corresponding aryl-hydroxy compounds using dicyclohexylcarbodiimide in the presence of a suitable base, for example, pyridine or triethylamine, in an inert solvent. Suitable solvents include methylene chloride, ethylene chloride, chloroform, ethyl acetate, tetrahydrofuran, etc., preferably chloroform. The reaction is carried out at temperatures of $-30°0$ C. to $+50°$ C., preferably about $+10°$ C.

The prostaglandin derivatives of Formula I wherein $R_1$ is hydrogen can be conventionally converted into salts using suitable amounts of the corresponding inorganic bases under normal neutralization conditions. For example, when dissolving the corresponding PG acids in water containing a stoichiometric quantity of the base, the solid inorganic salt can be obtained after evaporation of the water or after the addition of a water-miscible solvent, for example, alcohol or acetone.

To produce an amine salt, which is also done in the conventional manner, the PG acid is dissolved, for example, in a suitable solvent, e.g., ethanol, acetone, diethyl ether or benzene, and at least a stoichiometric amount of the amine is added to this solution. During this process, the salt is ordinarily obtained in the solid form or is isolated in conventional fashion after evaporation of the solvent.

The functional modification of the free OH-groups also takes place according to conventional methods known to those skilled in the art. To introduce the ether blocking groups, the reaction can be conducted, for example, with dihydropyran in methylene chloride or chloroform with the use of an acidic condensation agent, e.g., p-toluenesulfonic acid. The dihydropyran is utilized in excess, preferably twice to ten times the amount of the theoretical requirement. The reaction is normally terminated at 0° C.–30° C. after 15–30 minutes.

The acyl blocking groups are introduced by reacting a compound of Formula I in a conventional manner with a carboxylic acid derivative, e.g., an acid chloride, acid anhydride, etc.

The liberation of a functionally modified OH-group to obtain the free OH-containing compounds of Formula I similarly takes place according to conventional methods. For example, ether blocking groups can be split off in an aqueous solution of an organic acid, e.g., acetic acid, propionic acid, etc., or in an aqueous solution of an inorganic acid, e.g., hydrochloric acid. To improve solubility, a water-miscible, inert organic solvent can be suitably added. Suitable organic solvents include, for example, alcohols, such as methanol and ethanol, and ethers, such as dimethoxyethane, dioxane, and tetrahydrofuran. Tetrahydrofuran is preferably employed. The splitting-off step is conducted preferably at temperatures of 20° C.–80° C.

The splitting-off of the silyl ether blocking groups can be effected, for example, with tetrabutylammonium fluoride. Examples of suitable solvents include tetrahydrofuran, diethyl ether, dioxane, methylene chloride, etc. The splitting-off step is preferably conducted at temperatures of 0° C.–80° C.

The saponification of the acyl groups can be coonducted, for example, using alkali metal or alkaline earth carbonates or hydroxides in an alcohol or in an aqueous solution of an alcohol. Suitable alcohols include aliphatic alcohols, e.g., methanol, ethanol, butanol, etc., preferably methanol. Suitable alkali metal carbonates and hydroxides include those of potassium and sodium, the potassium salts being preferred. Examples of suitable alkaline earth carbonates and hydroxides include calcium carbonate, calcium hydroxide, and barium carbonate. The reaction generally takes place at −10° to +70° C., preferably at about 25° C.

The ketone of Formula II utilized as the starting material for the process described above can be readily prepared as follows:

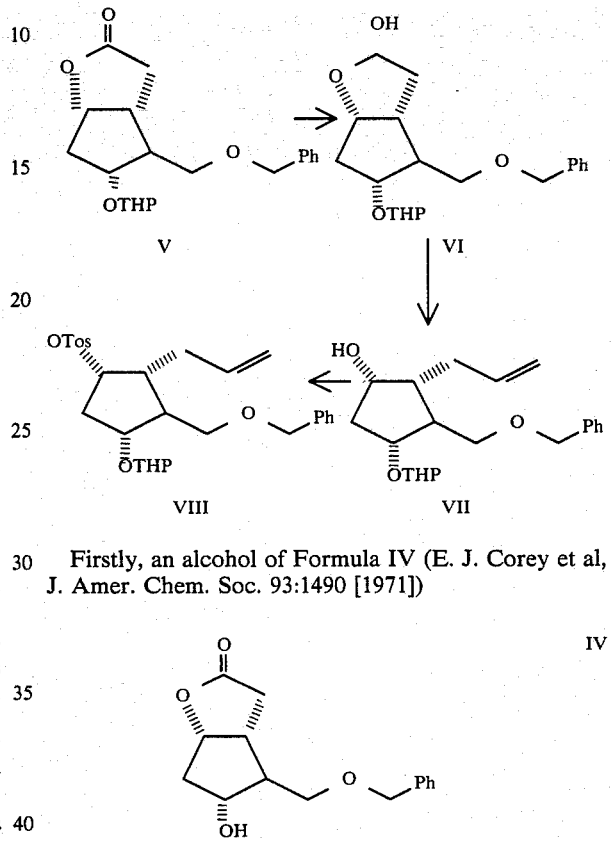

Firstly, an alcohol of Formula IV (E. J. Corey et al, J. Amer. Chem. Soc. 93:1490 [1971])

is converted into the tetrahydropyranyl ether V using dihydropyran in the presence of catalytic amounts of p-toluenesulfonic acid. The lactone V is reduced to the lactol VI using diisobutyl aluminum hydride at −70° C.; the lactol is converted into the olefin VII by Wittig reaction with triphenylphosphonium methylene. After conversion into the tosylate VIII with p-toluenesulfonyl chloride in the presence of pyridine, reaction with potassium nitrite in dimethyl sulfoxide yields the alcohol IX in the 9 β-configuration.

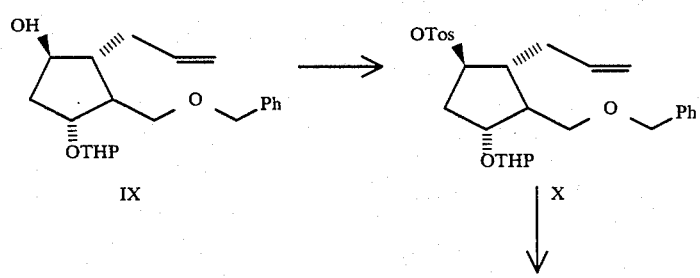

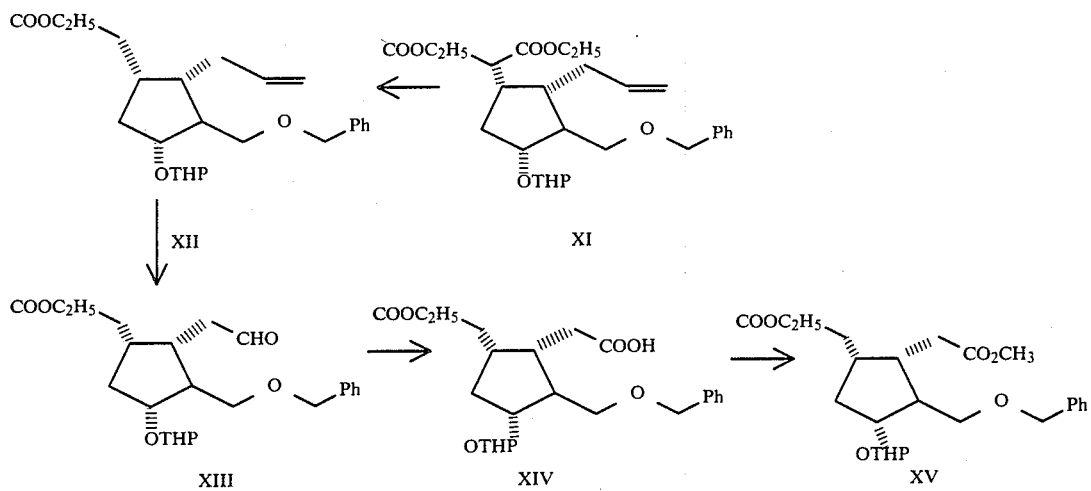

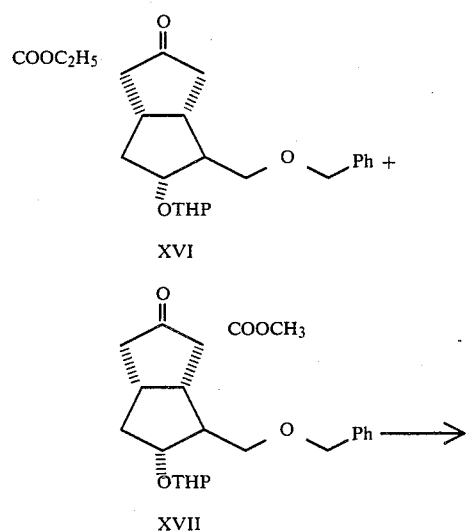

IX is converted into the tosylate X using p-toluenesulfonyl chloride in the presence of pyridine. Reaction with the diethyl ester of malonic acid in the presence of potassium tert-butylate produces the diester XI which is converted into the ester XII by decarbalkoxylation with sodium cyanide in dimethyl sulfoxide.

Oxidative splitting of the double bond in compound XII with sodium periodate in the presence of catalytic amounts of osmium tetroxide leads to the aldehyde XIII which is oxidized with Jones reagent to the acid XIV. The latter is then esterified to compound XV with diazomethane. By Dieckmann condensation of XV with potassium tert-butylate in tetrahydrofuran, a mixture of isomers of the ketocarboxylic acid esters XVI and XVII is obtained.

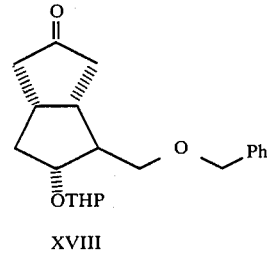

This mixture is converted into the ketone XVIII as the sole reaction product by means of a decarbalkoxylation with 1,4-diazabicyclo[2,2,2]octane in xylene.

Splitting off the tetrahydropyranyl ether blocking group yields the alcohol XIX which is esterified to the ester XX with benzoyl chloride in the presence of pyridine:

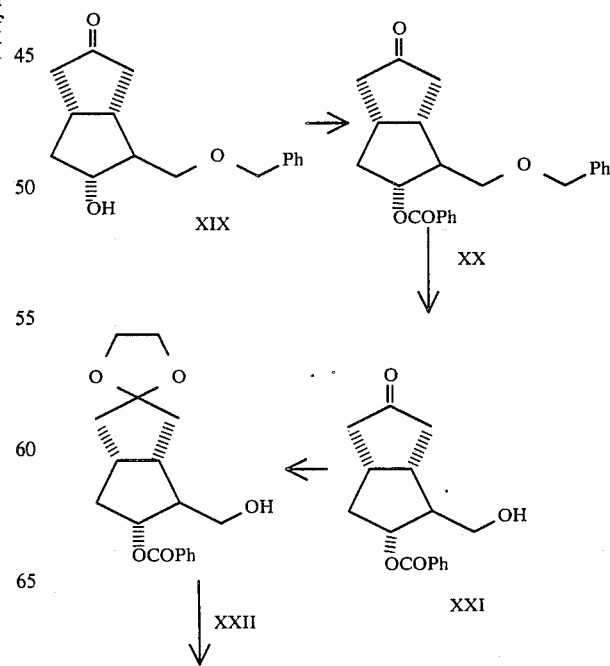

-continued

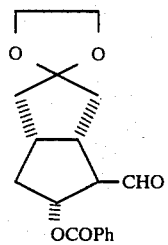

XXIII

Splitting of the benzyl ether by hydrogenolysis in the presence of catalytic amounts of an acid yields the alcohol XXI which is oxidized, after ketalization to the compound XXII, with Collins reagent to obtain the aldehyde XXIII.

This aldehyde is reacted with a phosphonate of Formula XXIV

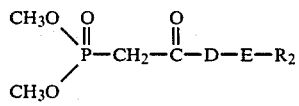

wherein D, E and $R_2$ are as defined above, in an olefin-forming reaction to a ketone of Formula XXV

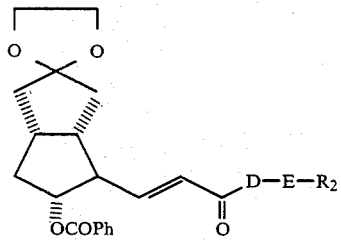
XXV

After reduction of the 15-keto group with zinc borohydride or sodium borohydride or reaction with alkyl magnesium bromide or alkyl lithium and separation of epimers, the 15α-alcohols XXVI are obtained (PG numbering):

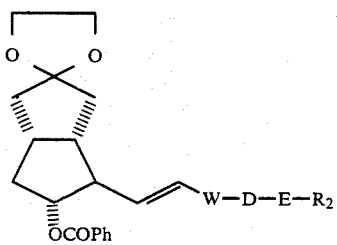
XXVI

After saponification of the ester group, for example, with potassium carbonate in methanol, and splitting the ketal with aqueous acetic acid, the ketone of Formula XXVII is obtained:

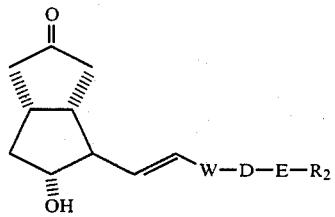
XXVII which, optionally after functional modification of the free hydroxy groups, for example, by etherification with dihydropyran or optionally hydrogenation of the double bond, is converted into the compounds of Formula II.

The compounds of this invention have a blood pressure lowering effect and a bronchodilatory activity. They are furthermore suitable for inhibiting thrombocyte aggregation. Consequently, the novel prostacyclin derivatives of Formula I are valuable pharmacological agents. Moreover, they exhibit, with a similar spectrum of effectiveness, a higher specificity as compared to corresponding prostaglandins, and, above all, a substantially longer efficacy. As compared to $PGI_2$, they are distinguished by a higher stability. The high tissue specificity of the novel prostaglandins can be established by a conventional test on smooth-muscle organs, such as, for example, the guinea pig ileum or the isolated rabbit trachea, where a substantially lower stimulation can be observed than for the application of natural prostaglandins of the E-, A, or F-type. The novel prostaglandin analogs possess properties typical of prostacyclins, such as, for example, lowering of the peripheral arterial and coronary vascular resistance, inhibition of thrombocyte aggregation and lysis of platelet clots, myocardial cytoprotection and thus a lowering of the systemic blood pressure without lowering at the same time the cardiac output and coronary blood perfusion and stroke, prophylaxis and therapy of coronary heart disease, coronary thrombosis, myocardial infarction, peripheral arterial disease, arteriosclerosis, thrombosis, therapy of shock, inhibition of bronchoconstriction, inhibition of gastric acid secretion and cytoprotection of the gastric and intestinalmucosa, antiallergic properties, lowering of pulmonary vascular resistance and of pulmonary blood pressure, promotion of kidney blood flow, application instead of heparin or as adjuvants in dialysis of haemo-filtration, conservation of blood plasma, especially of blood platelets, inhibition of labor pains, treatment of gestosis, increase of cerebral blood flow, etc. Additionally, the novel prostaglandin analogs display antiproliferative properties.

Upon intravenous injection into nonanesthetized, hypertonic rats in doses of 5, 20, and 100 μg/kg of body weight, the compounds of this invention display a stronger blood pressure lowering effect, and of a longer duration, than $PGE_2$ and $PGA_2$ compounds, without triggering diarrhea as do the $PGE_2$ compounds or cardiac arrythmias as do the $PGA_2$ compounds.

Upon intravenous injection into narcotized rabbits, the compounds of this invention, as compared to $PGE_2$ and $PGA_2$ compounds, display a stronger blood pressure lowering effect of a considerably longer duration, without affecting other smooth-muscle organs or organ functions.

The pharmacologically active compounds of this invention can be processed in accordance with conventional methods of galenic pharmacy to produce medicinal agents, especially for oral administration. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of this invention are dipensed in unit dosage form comprising 0.01-100 mg in a pharmaceutically acceptable carrier per unit dosage.

The dosage of the compounds according to this invention is 1-1500 mg/day when administered to human patients as drugs. for the treatment of the mentioned disease.

Thus, e.g., sterile, injectable, aqueous or oily solutions are utilized for parenteral administration. Suitable for oral application are, for example, tablets, dragees or capsules.

The invention thus also relates to medicinal agents comprising the compounds of this invention and customary excipients and vehicles.

The active agents of this invention can serve, in conjunction with the auxiliary agents known and customary in galenic pharmacy, for example, for the production of blood pressure lowering agents.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following examples, all temperatures are set forth uncorrected in degrees Celsius; unless otherwise indicated, all parts and percentages are by weight.

REFERENCE EXAMPLE 1

1(a)

(1S,5R,6S,7R)-6-Benzyloxymethyl-7-(tetrahydropyran-2-yloxy)-2-oxabicyclo[3,3,0]octan-3-one A solution of 14.5 g. of (1S,5R,6S,7R)-6-benzyloxymethyl-7-hydroxy-2-oxabicyclo[3,3,0]octan-3-one, 6 ml. of dihydropyran, and 40 mg. of p-toluenesulfonic acid in 300 ml. of absolute methylene chloride as agitated for one hour at 5°. Then the solution is diluted with ether, shaken with 4% sodium bicarbonate solution, washed neutral with water, dried over magnesium sulfate, and evaporated under vacuum. Yield: 21 g. of the tetrahydropyranyl ether as a colorless oil.

IR: 2950, 2860, 1770, 1458 cm$^{-1}$.

1(b)

(1S,3RS,5R,6S,7R)-6-Benzyloxymethyl-3-hydroxy-7-(tetrahydropyran-2-yloxy)-2-oxabicyclo[3,3,0]octane At −70° under argon, 160 ml. of a 1.2-molar solution of diisobutyl aluminum hydride in toluene is added dropwise to a solution of 21 g. of the product prepared according to Reference Example 1(a) in 940 ml. of absolute toluene. The mixture is stirred for 30 minutes at −70°, combined dropwise with 5 ml. of isopropanol, allowed to warm up to −10°, mixed with 70 ml. of water, agitated for 2 hours at room temperature, filtered, and evaporated under vacuum, thus obtaining 20 g. of the lactol as a colorless oil.

IR: 3600, 3400 (broad), 2950, 2860, 1457 cm$^{-1}$.

1(c)

(1S,2R,3S,4R)-3-Benzyloxymethyl-2-(prop-2-en-1-yl)-4-(tetrahydropyran-2-yloxy)cyclopentanol At 15° under argon, 77 ml. of a 1.04-molar solution of methylsulfinylmethyl sodium in DMSO is added dropwise to a solution of 28.6 g. of methyltriphenylphosphonium bromide in 75 ml. of absolute dimethyl sulfoxide (DMSO). The mixture is agitated for one hour at room temperature. Thereafter a solution of 7 g. of the lactol produced according to Reference Example 1(b) in 50 ml. of absolute DMSO is added thereto, and the mixture is stirred for 3 hours at room temperature. The mixture is then stirred into 500 ml. of ice water, extracted four times with respectively 200 ml. of a mixture of pentane/ether (1+1), the organic extract is washed neutral with water, dried over magnesium sulfate, and evaporated under vacuum. The residue is purified by chromatography on silica gel with pentane/ether gradients, thus obtaining 6.1 g. of the cyclopentanol as a colorless oil.

IR: 3500, 2940, 2855, 920, 968, 998 cm$^{-1}$.

1(d)

(1S,2R,3S,4R)-3-Benzyloxymethyl-2-(prop-2-en-1-yl)-1-tosyloxy-4-(tetrahydropyran-2-yloxy)cyclopentane A solution of 12.5 g. of the alcohol prepared according to Reference Example 1(c) in 36 ml. of pyridine is combined with 13.6 g. of p-toluenesulfonyl chloride and agitated for 2 days at room temperature under argon. The mixture is then combined with 6 ml. of ice water, stirred for 2 hours at room temperature, diluted with 0.6 l. of ether, and shaken, in succession, with water, ice-cold 4% sulfuric acid, water, 5% NaHCO$_3$ solution, and three times with water. The mixture is dried over magnesium sulfate and evaporated under vacuum, thus obtaining 17.3 g. of the tosylate as a colorless oil IR: 2950, 2863, 1600, 1365, 1175, 903 cm$^{-1}$.

1(e)

(1R,2R,3S,4R)-3-Bensyloxymethyl-2-(prop-2-en-1-yl)-4-(tetrahydropyran-2-yloxy)cyclopentanol A solution of 17 g. of the tosylate produced according to 1(d) in 500 ml. of DMSO is combined with 51 g.

of potassium nitrite and agitated for 2.5 hours at 65° under argon. The mixture is then poured on a 20% sodium chloride solution, extracted five times with respectively 250 ml. of a mixture of pentane/ether (1+1), the organic phase is washed three times with respectively 100 ml. of brine, dried over magnesium sulfate, and evaporated under vacuum. Chromatography of the residue on silica gel yields, with ether/pentane (3+2), 7.8 g. of the inverted alcohol as a colorless oil.

IR: 3600, 3450, 2950, 2864, 1000, 974, 918 cm$^{-1}$.

1(f)
(1R,2R,3S,4R)-3-Benzyloxymethyl-2-(prop-2-en-1-yl)-4-(tetrahydropyran-2-yloxy)-1-tosyloxycyclopentane Analogously to Reference Example 1(d), 6.8 g. of the alcohol prepared according to 1(e) yields 9.5 g. of the tosylate as a colorless oil.

IR: 2950, 2863, 1645, 1602, 1375, 1177, 975, 910 cm$^{-1}$.

1(g)
(1S,2S,3S,4R)-1-(bisethoxycarbonyl)-methyl-3-benzyloxymethyl-2-(prop-2-en-1-yl)-4-(tetrahydropyran-2-yloxy)cyclopentane A solution of 30.2 g. of malonic acid diethyl ester in 125 ml. of tert.-butanol is combined with 10.6 g. of potassium tert.-butylate and agitated for one hour at 60°-80°. Then a solution of 9.5 g. of the tosylate produced according to 1(f) in 45 ml. of tert.-butanol is added thereto and the mixture stirred for 26 hours under reflux and argon. The mixture is then diluted with ether, washed neutral with water, dried over magnesium sulfate, and evaporated under vacuum. The residue is freed of volatile components by silicate tube distillation at 0.1 torr [mm. Hg] and 60°-80°. Chromatography on silica gel with pentane/ethyl acetate (4+1) for purification yields 5.5 g. of the above diester as a colorless oil.

IR: 2950, 2860, 1750, 1730, 1642, 973, 915 cm$^{-1}$.

1(h)
(1R,2S,3S,4R)-1-Ethoxycarbonylmethyl-3-benzyloxymethyl-2-(prop-2-en-1-yl)-4-(tetrahydropyran-2-yloxy)cyclopentane 4.60 g. of the diester prepared according to Reference Example 1(g) and 1.06 g. of sodium cyanide in 30 ml. of DMSO are agitated for 20 hours at 150° under argon. The mixture is then diluted with 300 ml. of a mixture of ether/pentane (1+1), shaken three times with respectively 50 ml. of water, and dried over magnesium sulfate and evaporated under vacuum. Purification by chromatography on silica gel yields, with pentane/ethyl acetate (9+1), 2.80 g. of the monoester as a colorless oil.

IR: 2950, 2860, 1730, 1643, 973, 916 cm$^{-1}$.

1(i)
(1R,2S,3S,4R)-1-Ethoxycarbonylmethyl-3-benzyloxymethyl-2-formylmethyl-4-(tetrahydropyran-2-yloxy)-cyclopentane At 25°, a solution of 16 mg. of osmium tetroxide in 2 ml. of tetrahydrofuran is added to a solution of 2.5 g. of the ester prepared according to Reference Example 1(h) in 31 ml. of tetrahydrofuran and 7.8 ml. of water. The mixture is then combined within 45 minutes with incremental portions of 3.2 g. of sodium periodate, agitated for 30 minutes at 25°, filtered, diluted with ether, shaken once with dilute sodium bisulfite solution, and washed neutral with water. The mixture is dried over magnesium sulfate and evaporated under vacuum, thus obtaining 2.48 g. of the aldehyde as a light-yellow oil.

IR: 2950, 2860, 2730, 1725, 970 cm$^{-1}$.

1(j)
(1R,2S,3S,4R)-1-Ethoxycarbonylmethyl-3-benzyloxymethyl-2-carboxymethyl-4-(tetrahydropyran-2-yloxy)cyclopentane At 5°, 2.5 ml. of Jones reagent is added dropwise to a solution of 2.5 g. of the aldehyde prepared according to 1(i) in 60 ml. of acetone. The mixture is stirred for 45 minutes at 5°; then excess reagent is decomposed by the dropwise addition of isopropanol, and the mixture is stirred for 5 minutes, diluted with ether, and washed neutral with water. The product is dried over magnesium sulfate, evaporated under vacuum, and the residue is purified by column chromatography on silica gel. With pentane/ethyl acetate (3+2), 1.9 g. of the carboxylic acid is obtained as a colorless oil.

IR: 3500 (broad), 2950, 2860, 1725, 970 cm$^{-1}$.

1(k)
(1R,2S,3S,4R)-1-Ethoxycarbonylmethyl-3-benzyloxymethyl-2-methoxycarbonyl-4-(tetrahydropyran-2-yloxy)cyclopentane At ice bath temperature 7 ml. of an ethereal diazomethane solution is added dropwise to a solution of 1.3 g. of the acid produced according to Reference Example 1(j) in 30 ml. of methylene chloride. The mixture is agitated for 3 minutes and evaporated under vacuum, thus obtaining 1.3 g. of the methyl ester as a colorless oil.

IR: 2958, 2860, 1731, 970 cm$^{-1}$.

1(l)
(1R,5S,6S,7R)-6-Benzyloxymethyl-7-(tetrahydropyran-2-yloxy)bicyclo[3,3,0]octan-3-one A mixture of 1.3 g. of the diester prepared according to Reference Example 1(k) and 3 g. of potassium tert.-butylate in 60 ml. of tetrahydrofuran is agitated for 3 hours at room temperature under argon. The mixture is then acidified with 10% citric acid solution to pH 5, diluted with ether, and washed neutral with water. The mixture is dried over magnesium sulfate and evaporated under vacuum, thus obtaining 1.2 g. of a mixture of the stereoisomeric β-keto ester.

For decarboxylation purposes, the crude product is dissolved in 24 ml. of xylene, then 2.4 g. of 1,4-diazabicyclo[2,2,2]octane is added thereto, and the mixture is stirred for 4 hours at 160° bath temperature under argon. The mixture is then diluted with ether, shaken in succession with water, ice-cold 3% sulfuric acid, sodium bicarbonate solution, and water, dried over magnesium sulfate, and evaporated under vacuum, thus producing 980 mg. of the ketone as a light-yellow oil.

IR: 2935, 2860, 1735, 970 cm$^{-1}$.

1(m)
(1R,5S,7R)-6-Benzyloxymethyl-7-hydroxybicyclo[3,3,0]octan-3-one 0.9 g. of the ketone prepared according to Reference Example 1(l) is agitated for 3 hours at 45° with 17 ml. of a mixture of acetic acid/water/tetrahydrofuran (65/35/10) and then evaporated under vacuum. The residue is purified by chromatography on silica gel. With pentane/ethyl acetate (3+2), 0.68 g. of the alcohol is obtained as a colorless oil.

IR: 3540, 2935, 2860, 1739, 1095 cm$^{-1}$.

1(n)
(1R,5S,6S,7R)-7-Benzoyloxy-6-benzyloxymethylbicyclo[3,3,0]octan-3-one

A solution of 0.55 g. of the alcohol prepared according to Reference Example 1(m) in 4 ml. of pyridine is combined with 0.5 ml. of benzoyl chloride. The mixture is agitated for 4 hours at 25°, combined with 0.4 ml. of water, agitated for 2 hours, diluted with ether, and the mixture is shaken in succession with water, 5% sulfuric acid, water, 4% sodium bicarbonate solution, and three times with water. After drying over magnesium sulfate the mixture is evaporated under vacuum, thus obtaining 720 mg. of the benzoate as a colorless oil.

IR: 2945, 2860, 1739, 1713, 1602, 1588, 1276 cm$^{-1}$.

1(o)
(1R,5S,6S,7R)-7-Benzoyloxy-6-hydroxymethylbicyclo[3,3,0]octan-3-one

A solution of 680 mg. of the benzoate prepared according to Reference Example 1(n) in 10 ml. of ethyl acetate and 0.5 ml. of glacial acetic acid acid is combined with 120 mg. of palladium on charcoal (10%) and shaken for 8 hours under a hydrogen atmosphere. Filtration and evaporation of the solution under vacuum yields 600 mg. of an oily crude product, which is purified by chromatography on silica gel with pentane/ethyl acetate (1+1), and 395 mg. of the pure alcohol as a colorless oil.

IR: 3500, 2945, 1739, 1712, 1602, 1588, 1278 cm$^{-1}$.

1(p)
(1R,5S,6S,7R)-3,3-Ethylenedioxy-7-benzoyloxy-6-hydroxymethylbicyclo[3,3,0]octane 320 mg. of the alcohol prepared according to Reference Example 1(o), 0.5 ml. of ethylene glycol, 4 mg. of p-toluenesulfonic acid, and 10 ml. of benzene are agitated for 1.5 hours with the use of a water trap at reflux temperature. The mixture is cooled, diluted with ether, shaken once with 4% sodium bicarbonate solution, washed neutral with water, dried over magnesium sulfate, and evaporated under vacuum, thus obtaining 390 mg. of the ketal as a colorless oil.

IR: 3500, 2945, 2882, 1708, 1604, 1588, 1280, 948 cm$^{-1}$.

1(q)
(1R,5S,6R,7R)-3,3-Ethylenedioxy-7-benzoyloxy-6-formylbicyclo[3,3,0]octane Under agitation at 5°, a solution of 1.03 g. of the ketal prepared according to Reference Example 1(p) in 32 ml. of absolute methylene chloride is added dropwise to a solution of 5.4 g. of Collins reagent in 63 ml. of absolute methylene chloride; the mixture is stirred for 20 minutes at 5°. Then the mixture is diluted with ether, shaken three times with sodium bicarbonate solution and three times with brine, dried over magnesium sulfate, and evaporated under vacuum at 25°, thus obtaining 840 mg. of the aldehyde as a yellow oil.

IR: 2960, 2730, 1720, 1603, 1588, 1275, 948 cm$^{-1}$.

EXAMPLE 1
5-{(E)-(1S,5S,6R,7R)-7-Hydroxy-6-[(E)-3α-hydroxy-1-octenyl]bicyclo[3,3,0]octan-3-ylidene}-pentanoic Acid At 15° under argon, 12 ml. of a 1.04-molar solution of methylsulfinylmethyl sodium in DMSO is added dropwise to a solution of 3.04 g. of 4-carboxybutyltriphenylphosphonium bromide in 6 ml. of dry dimethyl sulfoxide (DMSO). The mixture is stirred for 30 minutes at room temperature. A solution of 495 mg. of (1R,5S,6R,7R)-7-(tetrahydropyran-2-yloxy)-6-[(E)-(3S)-3-(tetrahydropyran-2-yloxy)-1-octenyl]bicyclo[3,3,0]octan-3-one in 3 ml. of absolute DMSO is added dropwise to the red ylene solution, and the reaction mixture is stirred for 2 hours at 45°, whereafter it is poured on ice water, acidified to pH 4–5 with 10% citric acid solution, and extracted three times with methylene chloride. The organic phase is shaken with brine, dried over magnesium sulfate, and evaporated under vacuum. Chromatography of the residue on silica gel yields, with ether/pentane (3+2), 462 mg. of the olefin-formation product which, to split off the blocking groups, is stirred with 15 ml. of a mixture of acetic acid/water/tetrahydrofuran (65/35/10) for 20 hours at 25°. The mixture is evaporated under vacuum and the residue chromatographed on silica gel. With methylene chloride/isopropanol (95+5), the initial yield is 65 mg. of 5-{(Z)-(1S,5S,6R,7R)-7-Hydroxy-6-[(E)-(3S)-3-hydroxy-1-octenyl]bicyclo[3,3,0]octan-3-ylidene}-pentanoic acid (m.p. 95°), as well as, in the form of the more polar component, 103 mg. of the title compound as a colorless oil.

IR: 3600, 3450 (broad), 2940, 2865, 1712, 1604, 975 cm$^{-1}$

The starting material for the above title compound is prepared as follows:

1(a)
(1R,5S,6R,7R)-3,3-Ethylenedioxy-7-benzoyloxy-6-[(E)-3-oxo-1-octenyl)]bicyclo[3,3,0]octane At room temperature a solution of 664 mg. of 2-oxoheptylphosphonic acid dimethyl ester in 5.5 ml. of dimethoxyethane (DME) absolute is added dropwise to a suspension of 126 mg. of sodium hydride (55% suspension in oil) in 11 ml. of DME absolute. The mixture is agitated for 10 minutes, then 121 mg. of lithium chloride is added thereto, and the mixture is stirred for 2 hours at room temperature under argon. Then the mixture is combined at −20° with a solution of 755 mg. of the aldehyde prepared according to Reference Example 1(g) in 11 ml. of DME (absolute), and the mixture is stirred for 2.5 hours at room temperature under argon. Thereafter the reaction mixture is poured on 120 ml. of saturated ammonium chloride solution, extracted three times with ether, the organic extract is washed neutral with water, dried over magnesium sulfate, and evaporated under vacuum. The residue is purified by chromatography on silica gel. With ether/pentane (1+1), 795 mg. of the title compound is obtained as a colorless oil.

IR: 2949, 2862, 1715, 1670, 1628, 1275, 979, 948 cm$^{-1}$.

1(b)
(1R,5S,6R,7R)-3,3-Ethylenedioxy-7-benzoyloxy-6-[(E)-3α-hydroxy-1-octenyl]bicyclo[3,3,0]octane At −40° 420 mg. of sodium borohydride is added in incremental portions to a solution of 790 mg. of the ketone prepared according to Example 1(a) in 24 ml. of methanol, and the mixture is stirred under argon at −40° for one hour. Then the mixture is diluted with ether, washed neutral with water, dried over magnesium sulfate, and evaporated under vacuum. By column chromatography on silica gel with ether/pentane (7+3), 245 mg. of the title compound is initially obtained as a colorless oil. As the more polar component, 152 mg. of (1R,5S,6R,7R)-3,3-ethylenedioxy-7-benzoyloxy-6-[(E)-(3R)-3-hydroxy-1-octenyl]bicyclo[3,3,-0]octane is produced.

IR: 3610, 3400 (broad), 2940, 1715, 1604, 1588, 1279, 971, 948 cm$^{-1}$.

1(c)
(1R,5S,6R,7R)-3,3-Ethylenedioxy-7-hydroxy-6-[(E)-3α-hydroxy-1-octenyl]bicyclo[3,3,0]octane A mixture of 500 mg. of the α-alcohol prepared according to Example 1(b) and 333 mg. of potassium carbonate (anhydrous) in 35 ml. of methanol is agitated for 16 hours at room temperature under argon. The mixture is then concentrated under vacuum, diluted with ether, and washed neutral with brine. The mixture is dried over magnesium sulfate and evaporated under vacuum, thus obtaining 495 mg. of the title compound as a colorless oil (crude product).

IR: 3600, 3450 (broad), 2940, 975, 948 cm$^{-1}$.

1(d)
(1R,5S,6R,7R)-7-Hydroxy-6-[(E)-3α-hydroxy-1-octenyl]bicyclo[3,3,0]octan-3-one 495 mg. of the diol prepared according to Example 1(c) is agitated for 22 hours with 18 ml. of a mixture of acetic acid/tetrahydrofuran/water (65/10/35). The mixture is then evaporated under vacuum while adding toluene, the residue is dissolved in methylene chloride, shaken twice with brine, dried over magnesium sulfate, and evaporated under vacuum. The residue is chromatographed on silica gel with ethyl acetate/pentane (9+1), thus obtaining 282 mg. of the title compound as a colorless oil.

IR: 3660, 3610, 2940, 2870, 1739, 973 cm$^{-1}$.

1(e)
(1R,5S,6R,7R)-7-(Tetrahydropyran-2-yloxy)-6-[(E)-3α-(tetrahydropyran-2-yloxy)-1-octenyl]bicyclo[3,3,0]octan-3-one A solution of 260 mg. of the ketone prepared according to Example 1(d), 0.36 ml. of dihydropyran, and 2.5 mg. of p-toluenesulfonic acid in 11 ml. of methylene chloride is agitated for 20 minutes at 5°. Then the mixture is diluted with ether, shaken with 4% sodium bicarbonate solution, washed neutral with water, dried over magnesium sulfate, and evaporated under vacuum, thus obtaining 490 mg. of the bis(tetrahydropyranyl)ether which is used without further purification for the Wittig reaction.

IR: 2955, 2862, 1739, 970 cm$^{-1}$.

EXAMPLE 2
5-{(E)-(1S,5S,6R,7R)-7-Hydroxy-6-[(E)-(4RS)-3α-hydroxy-4-methyl-1-octenyl]bicyclo[3,3,0]octan-3-ylidene}-pentanoic Acid At 15° under argon, 24 ml. of a 1.04-molar solution of methylsulfinylmethyl sodium in DMSO is added dropwise to 6.1 g. of 4-carboxybutyltriphenylphosphonium bromide in 12 ml. of DMSO absolute, and the mixture is agitated for 30 minutes at room temperature. A solution of 0.95 g. of (1R,5S,6R,7R)-7-tetrahydropyran-2-yloxy)-6-[(E)-(4RS)-4-methyl-3α-(tetrahydropyran-2-yloxy)-1-octenyl]bicyclo[3,3,0]octan-3-one in 6 ml. of absolute DMSO is added dropwise to the red ylene solution and the mixture is agitated for 2 hours at 45°. The reaction mixture is poured on ice water, acidified to pH 4–5 with 10% citric acid solution, and extracted three times with methylene chloride. The organic phase is shaken with brine, dried over magnesium sulfate, and evaporated under vacuum. Chromatography of the residue on silica gel yields, with ether/pentane (3+2), 0.89 g. of the olefin-formation product, which is stirred with 28 ml. of a mixture of acetic acid/water/tetrahydrofuran (65/35/10) to split off the blocking groups. The product is evaporated under vacuum and the residue chromatographed on silica gel. With methylene chloride/isopropanol (95+5), 142 mg. of 5-{(Z)-(1S,5S,6R,7R)-7-hydroxy-6-[(E)-(4RS)-3α-hydroxy-4-methyl-1-octenyl]bicyclo[3,3,0]octan-3-ylidene}-pentanoic acid is initially obtained, and, as the more polar component, 230 mg. of the title compound is produced as a colorless oil.

IR: 3610, 3440 (broad), 2940, 2860, 1712, 976 cm$^{-1}$.

The starting material for the above title compound is prepared as follows:

2(a)
(1R,5S,6R,7R)-3,3-Ethylenedioxy-7-benzoyloxy-6-[(E)-(4RS)-4-methyl-3-oxo-1-octenyl]bicyclo[3,3,0]octane Analogously to Example 1(a), 1.62 g. of the title compound is obtained as a colorless oil from 1.5 g. of the aldehyde prepared accordingly to Reference Example 1(q) and 1.3 g. of 3-methyl-2-oxoheptanephosphonic acid dimethyl ester.

IR: 2940, 2860, 1715, 1672, 1628, 1275, 978, 948 cm$^{-1}$.

2(b)
(1R,5S,6R,7R)-3,3-Ethylenedioxy-7-benzoyloxy-6-[(E)-(4RS)-3α-hydroxy-4-methyl-1-octenyl]bicyclo[3,3,0]octane At −40° 850 mg. of sodium borohydride is added in incremental portions to a solution of 1.50 g. of the ketone prepared according to Example 2(a) in 48 ml. of methanol; the mixture is stirred for one hour at −40° under argon. The mixture is then diluted with ether, washed neutral with water, dried over magnesium sulfate, and evaporated under vacuum. By column chromatography on silica gel with ether/pentane (7+3), 520 mg. of the title compound (3α-hydroxy) is initially obtained and, as the more polar component, 320 mg. of the isomeric 3β-hydroxy-configured compound is produced.

IR: 3600, 3420 (broad), 2940, 1715, 1603, 1588, 1278, 972, 948 cm$^{-1}$.

2(c)
(1R,5S,6R,7R)-3,3-Ethylenedioxy-7-hydroxy-6-[(E)-(4RS)-3α-hydroxy-4-methyl-1-octenyl]bicyclo[3,3,0]octane A mixture of 510 mg. of the α-alcohol prepared according to Example 2(b) and 330 mg. of potassium carbonate in 35 mg. of methanol is agitated for 18 hours at room temperature under argon. The mixture is then concentrated under vacuum, diluted with ether, and washed neutral with brine. Then, the mixture is dried over magnesium sulfate and evaporated under vacuum, yielding 485 mg. of the title compound as a colorless oil (crude product).

IR: 3600, 3430 (broad), 2945, 976, 948 cm$^{-1}$.

2(d)
(1R,5S,6R,7R)-Hydroxy-6-[(E)-(4RS)-3α-hydroxy-4-methyl-1-octenyl]bicyclo[3,3,0]octan-3-one Analogously to Example 1(d), 485 mg. of the diol produced according to Example 2(c) yields 295 mg. of the title compound as an oil.

IR: 3600, 3400 (broad), 2940, 2865, 1740, 973 cm$^{-1}$.

2(e)
(1R,5S,6R,7R)-7-(Tetrahydropyran-2-yloxy)-6-[(E)-(4RS)-4-methyl-3α-(tetrahydropyran-2-yloxy)-1-octenyl]bicyclo[3,3,0]octan-3-one Analogously to Example 1(e), 280 mg. of the ketone prepared according to Example 2(d) yields 460 mg. of the bis(tetrahydropyranyl)ether, which is used for the Wittig reaction without further purification.

IR: 2960, 2860, 1740, 972 cm$^{-1}$.

EXAMPLE 3

5-{(E)-(1S,5S,6R,7R)-7-Hydroxy-6-[(E)-(4RS)-4-fluoro-3α-hydroxy-1-octenyl]bicyclo[3,3,0]octan-3-ylidene}-pentanoic Acid At 15° under argon 18 ml. of a 1.04-molar solution of methylsulfinylmethyl sodium in DMSO is added dropwise to a solution of 4.55 g. of 4-carboxybutyltriphenylphosphonium bromide in 10 ml. of absolute DMSO, and the mixture is stirred for 30 minutes at room temperature. A solution of 745 mg. of (1R,5S,6R,7R)-7-tetrahydropyran-2-yloxy)-6-[(E)-(4RS)-4-fluoro-3α-(tetrahydropyran-2-yloxy)-1-octenyl]bicyclo[3,3,0]octan-3-one in 5 ml. of absolute DMSO is added dropwise to the red ylene solution, and the mixture is agitated for 2 hours at 45°. The reaction mixture is poured on ice water, acidified to pH 4-5 with 10% citric acid solution, and extracted three times with methylene chloride. The organic phase is shaken with brine, dried over magnesium sulfate, and evaporated under vacuum. Chromatography of the residue on silica gel yields, with ether/pentane (3+2), 620 mg. of the olefin-formation product which is agitated, to split off the blocking groups, with 22 ml. of a mixture of acetic acid/water/tetrahydrofuran (65/35/10) for 20 hours at 25°. The mixture is evaporated under vacuum and the residue chromatographed on silica gel. With methylene chloride/isopropanol (95+5), the initial product is 122 mg. of 5-{(Z)-(1S,5S,6R,7R)-7-hydroxy-6-[(E)-(4RS)-4-fluoro-3α-hydroxy-1-octenyl]bicyclo[3,3,0]octan-3-ylidene}-pentanoic acid as well as, in the form of the more polar component, 208 .mg. of the title compound as a colorless oil.

IR: 3600, 3440 (broad), 2945, 2860, 1713, 976 cm$^{-1}$.

The starting material for the above title compound is prepared as follows:

3(a)
(1R,5S,6R,7R)-3,3-Ethylenedioxy-7-benzoyloxy-6-[(E)-(4RS)-4-fluoro-3-oxo-1-octenyl]bicyclo[3,3,0]octane Analogously to Example 1(a), 765 mg. of the aldehyde prepared according to Reference Example 1(q) and 665 mg. of 3-fluoro-2-oxoheptanephosphonic acid dimethyl ester yield 620 mg. of the title compound as a colorless oil.

IR: 2945, 2860, 1715, 1670, 1630, 1276, 979, 948 cm$^{-1}$.

3(b)
(1R,5S,6R,7R)-3,3-Ethylenedioxy-7-benzoyloxy-6-[(E)-(4RS)-4-fluoro-3α-hydroxy-1-octenyl]bicyclo[3,3,0]octane Analogously to Example 1(b), 410 mg. of the ketone produced according to Example 3(a) and 230 mg. of sodium borohydride yield 146 mg. of the title compound as a colorless oil.

IR: 3600, 3410 (broad), 2945, 2865, 1715, 1604, 1590, 1278, 974, 948 cm$^{-1}$.

3(c)
(1R,5S,6R,7R)-3,3-Ethylenedioxy-7-hydroxy-6-[(E)-(4RS)-4-fluoro-3α-hydroxy-1-octenyl]bicyclo[3,3,0]octane In analogy to Example 1(c), 525 mg. of the α-alcohol prepared according to Example 3(b) and 340 mg. of potassium carbonate yield 490 mg. of the title compound as an oil.

IR: 3600, 3400 (broad), 2950, 2865, 976, 948 cm$^{-1}$.

3(d)
(1R,5S,6R,7R)-7-Hydroxy-6-[(E)-(4RS)-4-fluoro-3α-hydroxy-1-octenyl]bicyclo[3,3,0]octan-3-one Analogously to Example 1(d), 470 mg. of the diol prepared according to Example 3(c) yields 285 mg. of the title compound in the form of an oil.

IR: 3600, 3420 (broad), 2945, 2865, 1740, 975 cm$^{-1}$.

3(e)
(1R,5S,6R,7R)-7-(Tetrahydropyran)-2-yloxy)-6-[(E)-(4RS)-4-fluoro-3α-(tetrahydropyran-2-yloxy)-1-octenyl]bicyclo[3,3,0]octan-3-one Analogously to Example 1(e), 285 mg. of the ketone produced by following Example 3(d) yields 470 mg. of the bis(tetrahydropyranyl)ether (crude product) which is used for the Wittig reaction without further purification.

IR: 2960, 2860, 1740, 975 cm$^{-1}$.

EXAMPLE 4

5-{(E)-(1S,5S,6R,7R)-7-Hydroxy-6-[(E)-3α-hydroxy-4,4-methylene-1-octenyl]bicyclo[3,3,0]octan-3-ylidene}-pentanoic Acid At 15° under argon, 36 ml. of a 1.04-molar solution of methylsulfinylmethyl sodium in DMSO is added dropwise to 9.2 g. of 4-carboxybutyltriphenylphosphonium bromide in 20 ml. of absolute DMSO, and the mixture is agitated for 30 minutes at room temperature. A solution of 1.45 g. of (1R,5S,6R,7R)-7-tetrahydropyran-2-yloxy)-6-[(E)-4,4-methylene-3α-(tetrahydropyran-2-yloxy)-1-octenyl]bicyclo[3,3,0]octan-3-one in 10 ml. of DMSO is added dropwise to the red ylene solution, and the mixture is stirred for 2 hours at 45°. The reaction mixture is poured on ice water, acidified to pH 5 with 10% citric acid solution, and extracted three times with methylene chloride. The organic phase is shaken with brine, dried over magnesium sulfate, and evaporated under vacuum. Chromatography of the residue on silica gel yields, with ether/pentane (3+2), 1.38 g. of the olefin-formation product which, to split off the blocking groups, is stirred with 35 ml. of a mixture of acetic acid/water/tetrahydrofuran (65/35/10). The mixture is then evaporated under vacuum and the residue chromatographed on silica gel. With methylene chloride/isopropanol (95+5), the initial product is 210 mg. of 5-{(Z)-(1S,5S,6R,7R)-7-hydroxy-6-[(E)-3α-hydroxy-4,4-methylene-1-octenyl]bicyclo[3,3,0]octan-3-ylidene}-pentanoic acid, and, as the more polar component, 295 mg. of the title compound is obtained as a colorless oil.

IR: 3600, 3450 (broad), 2945, 2865, 1712, 976 cm$^{-1}$.

The starting material for the above title compound is prepared as follows:

4(a)
(1R,5S,6R,7R)-3,3-Ethylenedioxy-7-benzoyloxy-6-[(E)-4,4-methylene-3-oxo-1-octenyl]bicyclo[3,3,0]octane Analogously to Example 1(a), 1.48 g. of the aldehyde produced according to Reference Example 1(q) and 1.3 g. of 3,3-methylene-2-oxoheptanephosphonic acid dimethyl ester yield 1.55 g. of the title compound as a colorless oil.

IR: 2940, 2860, 1715, 1670, 1630, 1275, 978 cm$^{-1}$.

4(b)
(1R,5S,6R,7R)-3,3-Ethylenedioxy-7-benzoyloxy-6-[(E)-3α-hydroxy-4,4-methylene-1-octenyl]bicyclo[3,3,0]octane In analogy to Example 1(b), 1.45 g. of the ketone prepared according to Example 4(a) and 850 mg. of sodium borohydride yield 510 mg. of the title compound as a colorless oil.

IR: 3600, 3400 (broad), 2945, 2860, 1715, 1603, 1590, 1277, 973, 948 cm$^{-1}$.

4(c)
(1R,5S,6R,7R)-3,3-Ethylenedioxy-7-hydroxy-6-[(E)-3α-hydroxy-4,4-methylene-1-octenyl]bicyclo[3,3,0]octane Analogously to Example 1(c), 490 mg. of the α-alcohol prepared according to Example 4(b) and 320 mg. of potassium carbonate yield 470 mg. of the title compound as a colorless oil.

IR: 3600, 3400 (broad), 2940, 2860, 976 cm$^{-1}$.

4(d)
(1R,5S,6R,7R)-7-Hydroxy-6-[(E)-3α-hydroxy-4,4-methylene-1-octenyl]bicyclo[3,3,0]octan-3-one Analogously to Example 1(d), 470 mg. of the diol prepared according to Example 4(c) produces 280 mg. of the title compound as an oil.

IR: 3600, 3400 (broad), 2945, 2860, 1740, 974 cm$^{-1}$.

4(e)
(1R,5S,6R,7R)-7-(Tetrahydropyran-2-yloxy)-6-[(E)-4,4-methylene-3α-(tetrahydropyran-2-yloxy)-1-octenyl]bicyclo[3,3,0]octan-3one In analogy to Example 1(e), 270 mg. of the ketone prepared according to Example 4(d) yields 440 mg. of the bis(tetrahydropyranyl)ether which is used for the Wittig olefin-forming reaction without further purification.

IR: 2960, 2860, 1739, 975 cm$^{-1}$.

EXAMPLE 5

5-{(E)-(1S,5S,6R,7R)-7-Hydroxy-6-[(E)-3α-hydroxy-1-nonenyl]bicyclo[3,3,0]octan-3-ylidene}-pentanoic Acid At 15° under argon, 13.2 ml. of a 1.04-molar solution of methylsulfinylmethyl sodium in DMSO is added dropwise to a solution of 3.34 g. of 4-carboxybutyltriphenylphosphonium bromide in 6.5 ml. of absolute DMSO. After 15 minutes, a solution of 500 mg. of (1R,5S,6R,7R)-7-(tetrahydropyran-2-yloxy)-6-[(E)-3α-(tetrahydropyran-2-yloxy)-1-nonenyl]bicyclo[3,3,0]octan-3-one in 3 ml. of absolute DMSO is added dropwise to this ylene solution, and the mixture is heated for 2 hours to 45°-50°. The mixture is then poured on ice water, acidified to pH 5 with citric acid, and extracted with methylene chloride. The extract is shaken with brine, dried over magnesium sulfate, and evaporated under vacuum. Chromatography of the residue on silica gel with ether/pentane mixture yields 435 mg. of a yellow oil, which is agitated to split off the blocking groups with 15 ml. of a mixture of acetic acid/water/tetrahydrofuran (65/35/10) for 16 hours at 40°. After evaporation of the solution, the residue is chromatographed on silica gel with methylene chloride/isopropanol (95+5). Yield: 80 mg. of 5-{(Z)-(1S,5S,6R,7R)-7-hydroxy-6-[(E)-3α-hydroxy-1-nonenyl]bicyclo[3,3,0]octan-3-ylidene}-pentanoic acid and, as the more polar component, 120 mg. of the title compound as a colorless, viscous oil.

IR: 3600, 3455 (broad), 2945, 2865, 1710, 978 cm$^{-1}$.

The starting material for the title compound is produced as described below:

5(a)
(1R,5S,6R,7R)-3,3-Ethylenedioxy-7-benzoyloxy-6-[(E)-3-oxo-1-nonenyl]bicyclo[3,3,0]octane 252 mg. of sodium hydride (55% strength) is suspended in 25 ml. of absolute dimethoxyethane, and at 15° 1.39 g. of 2-oxooctylphosphone acid dimethyl ester dissolved in 10 ml. of dimethoxyethane is added dropwise thereto. The mixture is stirred for 10 minutes, combined with 245 mg. of lithium chloride, and, after one hour at −20°, a solution of 1.51 g. of the aldehyde prepared according to Reference Example 1(q) in 25 ml. of absolute dimethoxyethane is added dropwise thereto. The mixture is then stirred for 2 hours at 10°-15°, poured on 250 ml. of saturated ammonium chloride solution, extracted repeatedly with ether, the organic extract washed with brine, dried over magnesium sulfate, and evaporated under vacuum. The residue is purified by chromatography on silica gel with ether/hexane mixtures. Yield: 1.49 g. of the above-mentioned ketone in the form of an oil.

IR: 2945, 2860, 1715, 1670, 1630, 1275, 978, 948 cm$^{-1}$.

5(b)
(1R,5S,6R,7R)-3,3-Ethylenedioxy-7-benzoyloxy-6-[(E)-3α-hydroxy-1-nonenyl]bicyclo[3,3,0]octane Under agitation at −40°, 800 mg. of sodium borohydride is added in incremental portions to a solution of 1.44 g. of the ketone prepared according to Example 5(a) in 40 ml. of methanol; the mixture is stirred for one hour at −40°, diluted with 200 ml. of ether, washed neutral with brine, dried over magnesium sulfate, and evaporated under vacuum. The mixture of the epimeric alcohols is separated by chromatography on silica gel with hexane/ether mixtures, thus obtaining as the nonpolar component 576 mg. of the desired (3S)-alcohol as an oil, as well as, in the form of the more polar component, 490 ml. of the (3R)-alcohol, likewise as an oil.

IR: 3600, 3400 (broad), 2945, 1715, 1602, 1588, 1275, 975, 948 cm$^{-1}$.

5(c)
(1R,5S,6R,7R)-3,3-Ethylenedioxy-7-hydroxy-6-[(E)-3α-hydroxy-1-nonenyl]bicyclo[3,3,0]octane 500 mg. of the (3S)-alcohol from Example 5(b) is stirred in 35 ml. of methanol with 315 mg. of potassium carbonate for 16 hours at 20°. After concentration under vacuum, the mixture is diluted with 200 ml. of ether, washed neutral with water, dried over magnesium sulfate, and evaporated under vacuum. The crude product is used in the next stage without further purification.

5(d)
(1R,5S,6R,7R)-7-Hydroxy-6-[(E)-3α-hydroxy-1-nonenyl]bicyclo[3,3,0]octan-3-one The crude product from Example 5(c) is stirred for 22 hours with 20 ml. of a mixture of acetic acid/water/tetrahydrofuran (65/35/10), evaporated under vacuum with the addition of toluene, and the residue is chromatographed on silica gel with ethyl acetate/hexane mixtures, thus obtaining 270 mg. of the above-mentioned ketone as an oil.

IR: 3600, 2945, 2870, 1740, 975 cm$^{-1}$.

5(e)
(1R,5S,6R,7R)-7-(Tetrahydropyran-2-yloxy)-6-[(E)-3α-(tetrahydropyran-2-yloxy)-1-nonenyl]bicyclo[3,3,0]octan-3-one 250 mg. of the ketone from Example 5(d) is stirred in 10 ml. of methylene chloride with 0.35 ml. of dihydropyran and 2.5 mg. of p-toluenesulfonic acid for 30 minutes at 0°–5°. Thereafter the mixture is diluted with 100 ml. of methylene chloride, shaken with sodium bicarbonate solution and brine, dried over magnesium sulfate, and evaporated under vacuum, thus obtaining 475 mg. of the bis(tetrahydropyranyl)ether as a yellow oil.

IR: 2955, 2860, 1740, 972 cm$^{-1}$.

EXAMPLE 6

5-{(E)-(1S,5S,6R,7R)-7-Hydroxy-6-[(E)-(4RS)-3α-hydroxy-4-methyl-1-nonenyl]bicyclo[3,3,0]octan-3-ylidene}-pentanoic Acid Analogously to Example 5, 420 mg. of (1R,5S,6R,7R)-7-(tetrahydropyran-2-yloxy)-6-[(E)-(4RS)-4-methyl-3α-(tetrahydropyran-2-yloxy)-1-nonenyl]bicyclo[3,3,0]octan-3-one yields 95 mg. of the title compound and 85 mg. of the Z-isomer 5-{(Z)-(1S,5S,6R,7R)-7-hydroxy-6-[(E)-(4RS)-3α-hydroxy-4-methyl-1-nonenyl]bicyclo[3,3,0]octan-3-ylidene}-pentanoic acid.

IR (E-isomers): 3600, 3450 (broad), 2945, 2860, 1710, 978 cm$^{-1}$.

The starting material for the title compound is produced as follows:

6(a)
(1R,5S,6R,7R)-3,3-Ethylenedioxy-7-benzoyloxy-6-[(E)-4-methyl-3-oxo-1-nonenyl]bicyclo[3,3,0]octane In analogy to Example 5(a), 2 g. of (1R,5S,6R,7R)-3,3-ethylenedioxy-7-benzoyloxy-6-formylbicyclo[3,3,0]octane yields, with the 3-methyl-2-oxooctylphosphonic acid dimethyl ester, 2.01 g. of the above-mentioned ketone as a viscous oil.

IR: 2950, 2860, 1715, 1670, 1630, 1602, 1275, 978, 948 cm$^{-1}$.

6(b)
(1R,5S,6R,7R)-3,3-Ethylenedioxy-7-benzoyloxy-6-[(E)-(4RS)-3α-hydroxy-4-methyl-1nonenyl]bicyclo[3,3,-0]octane Analogously to Example 5(b), 1.95 g. of the ketone prepared according to Example 6(a) yields 800 mg. of the above (3R)-α-alcohol and, as the more polar component, 730 mg. of the (3S)-β-alcohol.

IR: 3600, 3400 (broad), 2950, 1715, 1602, 1588, 1270, 978, 948 cm$^{-1}$.

6(c)
(1R,5S,6R,7R)-3,3-Ethylenedioxy-7-hydroxy-6-[(E)-(4RS)-3α-hydroxy-4-methyl-1-nonenyl]bicyclo[3,3,-0]octane In analogy to Example 5(c), 790 mg. of the (3R)-α-alcohol prepared according to Example 6(b) yields 750 mg. of the above diol as a crude product.

6(d)
(1R,5S,6R,7R)-7-Hydroxy-6-[(E)-(4RS)-3α-hydroxy-4-methyl-1-nonenyl]bicyclo[3,3,0]octan-3-one Analogously to Example 5(d), 730 mg. of the diol prepared according to Example 6(c) yields 420 mg. of the above ketone as a colorless oil.

IR: 3600, 2950, 2870, 1740, 978 cm$^{-1}$.

6(e)
(1R,5S,6R,7R)-7-(Tetrahydropyran-2-yloxy)-6-[(E)-(4RS)-4-methyl-3α-(tetrahydropyran-2-yloxy)-1-nonenyl]bicyclo[3,3,0]octan-3-one Analogously to Example 5(e), 700 mg. of the ketone prepared as in Example 6(d) yields 950 mg. of the above bis(tetrahydropyranyl)ether as an oil.

IR: 2950, 2860, 1740, 978 cm$^{-1}$.

EXAMPLE 7

5-{(E)-(1S,5S,6R,7R)-7-Hydroxy-6-[(E)-3α-hydroxy-4-phenyl-1-butenyl]bicyclo[3,3,0]octan-3-ylidene}-pentanoic Acid A solution of 2.21 g. of 4-carboxybutyltriphenylphosphonium bromide in 5 ml. of absolute DMSO is combined at 15° with 9.5 ml. of a 1.04-molar solution of methylenesulfinyl sodium in DMSO. After 15 minutes, 440 mg. of (1R,5S,6R,7R)-7-(tetrahydropyran-2-yloxy)-6-[(E)-4-phenyl-3α-(tetrahydropyran-2-yloxy)-1-butenyl]bicyclo[3,3,0]-octan-3-one, dissolved in 3 ml. of absolute DMSO, is added to the reaction mixture, and the latter is stirred for 2 hours at 50°, then poured on ice water, and adjusted to pH 4.5 with citric acid. The mixture is extracted with methylene chloride, the extract is shaken with brine, dried over magnesium sulfate, and evaporated under vacuum. After purification by chromatography on silica gel with hexane/ether mixtures, the product is reacted with acetic acid to split off the blocking groups (analogously to Example 5). Purification by chromatography on silica gel with methylene chloride/isopropanol (95+5) produces 75 mg. of 5-{(Z)-(1S,5S,6R,7R)-7-hydroxy-6-[(E)-3α-hydroxy-4-phenyl-1-butenyl]bicyclo[3,3,0]octan-3-ylidene}-pentanoic acid and, as the more polar component, 110 mg. of the title compound as a colorless oil.

IR: 3600, 3450 (broad), 2945, 2860, 1710, 1602, 978 cm$^{-1}$

The starting material for the title compound is prepared as follows:

7(a)
(1R,5S,6R,7R)-3,3-Ethylenedioxy-7-benzoyloxy-6-[(E)-3-oxo-4-phenyl-1-butenyl]bicyclo[3,3,0]octan In analogy to Example 5(a), 2.5 g. of (1R,5S,6R,7R)-3,3-ethylenedioxy-7-benzoyloxy-6-formylbicyclo[3,3,-0]octane produces, by reaction with the sodium salt of 2-oxo-3-phenylpropylphosphonic acid dimethyl ester, 2.45 g. of the above ketone as an oil.

IR: 2955, 2870, 1712, 1670, 1632, 1600, 1275, 975, 948 cm$^{-1}$.

7(b)
(1R,5S,6R,7R)-3,3-Ethylenedioxy-7-benzoyloxy-6-[(E)-3α-hydroxy-4-phenyl-1-butenyl]bicyclo[3,3,0]octane Analogously to Example 5(b), 2.40 g. of the ketone prepared according to Example 7(a) yields 1.05 g. of the above (3S)-α-alcohol and, as the more polar component, 0.95 g. of the (3R)-β-alcohol.

IR: 3600, 3400 (broad), 2950, 2865, 1712, 1602, 1588, 1270, 978, 948 cm$^{-1}$.

7(c)
(1R,5S,6R,7R)-3,3-Ethylenedioxy-7-hydroxy-6-[(E)-3α-hydroxy-4-phenyl-1-butenyl]bicyclo[3,3,0]octane Analogously to Example 5(c), 1.02 g. of the (3S)-α-alcohol prepared according to Example 7(b) yields 800 mg. of the above diol as a crude product.

7(d)
(1R,5S,6R,7R)-7-Hydroxy-6-[(E)-3α-hydroxy-4-phenyl-1-butenyl]bicyclo[3,3,0]octan-3-one In analogy to Example 5(d), 800 mg. of the diol prepared according to Example 7(c) yields 530 mg. of the above ketone as a colorless oil.

IR: 3600, 2950, 2865, 1738, 1602, 975 cm$^{-1}$.

7(e)
(1R,5S,6R,7R)-7-(Tetrahydropyran-2-yloxy)-6-[(E)-4-phenyl-3α-(tetrahydropyran-2-yloxy)-1-butenyl]bicyclo[3,3,0]octan-3-one Analogously to Example 5(e), 500 mg. of the ketone prepared according to Example 7(d) yields 700 mg. of the above bis(tetrahydropyranyl)ether as an oil.

IR: 2950, 2860, 1738, 1602, 976 cm$^{-1}$.

EXAMPLE 8
5-{(E)-(1S,5S,6R,7R)-7-Hydroxy-6-[(4RS)-3α-hydroxy-4-methyl-1-octyl]bicyclo[3,3,0]octan-3-ylidene}-pentanoic Acid An ylene solution, prepared from 3 g. of 4-carboxybutyltriphenylphosphonium bromide analogously to Example 5, is combined with 450 mg. of (1R,5S,6R,7R)-7-(tetrahydropyran-2-yloxy)-6-[(4RS)-4-methyl-3α-(tetrahydropyran-2-yloxy)-1-octyl]bicyclo[3,3,0]octan-3-one, dissolved in 3 ml. of absolute DMSO. The mixture is stirred for 2 hours at 50°, then diluted with ice water, acidified to pH 4.5 with citric acid, and extracted repeatedly with methylene chloride. The extracts are combined, shaken with brine, dried over magnesium sulfate, and evaporated under vacuum. To remove the blocking groups, the crude product is agitated for 6 hours at 45° with 20 ml. of a mixture of acetic acid/water/tetrahydrofuran (65/35/10). After evaporation to dryness, the residue is chromatographed on silica gel with methylene chloride/1–5% isopropanol. Yield: 80 mg. of 5-{(Z)-(1S,5S,6R,7R)-7-hydroxy-6-[(4RS)-3α-hydroxy-4-methyl-1-octyl]bicyclo[3,3,0]octan-3-ylidene}-pentanoic acid, and, as the more polar component, 110 mg. of the title compound as a colorless oil.

IR: 3600, 3450 (broad), 2950, 2860, 1710 cm$^{-1}$.

The starting material for the title compound is prepared as follows:

8(a)
(1R,5S,6R,7R)-7-(Tetrahydropyran-2-yloxy)-6-[(4RS)-4-methyl-3α-(tetrahydropyran-2-yloxy)-1-octyl]bicyclo[3,3,0]octan-3-one A solution of 1 g. of (1R,5S,6R,7R)-7-(tetrahydropyran-2-yloxy)-6-[(E)-(4RS)-4-methyl-3α-(tetrahydropyran-2-yloxy)-1-ocetenyl]bicyclo[3,3,0]octan-3-one in 25 ml. of ethyl acetate is shaken with 100 mg. of palladium on charcoal (10%) under a hydrogen atmosphere for about one hour until 1 mole of hydrogen has been absorbed per mole of substrate. Filtration and evaporation of the solvent yields the above compound as a light-yellow oil.

IR: 2960, 2865, 1740 cm$^{-1}$.

EXAMPLE 9
5-[(E)-(1S,5S,6R,7R)-7-Hydroxy-6-(3α-hydroxy-1-nonyl)bicyclo[3,3,0]octan-3-ylidene]-pentanoic Acid An ylene solution, prepared from 3.5 g. of 4-carboxybutyltriphenylphosphonium bromide analogously to Example 5, is combined with 500 mg. of (1R,5S,6R,7R)-7-(tetrahydropyran-2-yloxy)-6-[3α-(tetrahydropyran-2-yloxy)-1-nonyl]bicyclo[3,3,0]octan-3-one, dissolved in 3 ml. of absolute DMSO. The mixture is stirred for 2 hours at 50°. After dilution with ice water and acidification to pH 4.5 with citric acid, the mixture is repeatedly extracted with methylene chloride. The combined extracts are shaken with brine, dried over magnesium sulfate, and evaporated under vaccum. To remove the blocking groups, the crude product is stirred for 6 hours at 45° with 20 ml. of a mixture of acetic acid/water/tetrahydrofuran (65/35/10). After evaporation to dryness the residue is chromatographed on silica gel with methylene chloride/1–5% isopropanol, thus obtaining 100 mg. of 5-[(Z)-(1S,5S,6R,7R)-7-hydroxy-6-(3α-hydroxy-1-nonyl)bicyclo[3,3,0]octan-3-ylidene]-pentanoic acid and, as the more polar component, 120 mg. of the title compound as a coloress oil.

IR: 3600, 3455 (broad), 2950, 2865, 1710 cm$^{-1}$.

The starting material for the title compound is obtained as follows:

9(a)
(1R,5S,6R,7R)-7-(Tetrahydropyran-2-yloxy)-6-[3α-(tetrahydropyran-2-yloxy)-1-nonyl]bicyclo[3,3,0]octan-3-one 800 mg. of (1R,5S,6R,7R)-7-(tetrahydropyran-2-yloxy)-6-[(E)-(3S)-3-(tetrahydropyran-2-yloxy-1-nonenyl]bicyclo[3,3,0]octan-3-one [prepared as set forth in Example 5(e)], dissolved in 20 ml. of ethyl acetate, is shaken with 80 mg. of palladium on charcoal (10%) under a hydrogen atmosphere until 1 mole of hydrogen has been absorbed per mole of substrate. After filtration and evaporation of the solvent, the above compound is obtained as an oil.

IR: 2965, 2865, 1740 cm$^{-1}$.

EXAMPLE 10
5-{(E)-(1S,5S,6R,7R)-7-Hydroxy-6-[(E)-3α-hydroxyoct-1-en-6-inyl]bicyclo[3,3,0]octan-3-ylidene}-pentanoic Acid At 15° under argon, 10.6 ml. of a 1.04-molar solution of methylsulfinylmethyl sodium in DMSO is added dropwise to a solution of 2.66 g. of 4-carboxybutyltriphenylphosphonium bromide in 6 ml. of absolute DMSO. The mixture is stirred for 30 minutes at room temperature. A solution of 430 mg. of (1R,5S,6R,7R)-7-(tetrahydropyran-2-yloxy)-6-[(E)-3α-(tetrahydropyran-2-yloxy)oct-1-en-6-inyl]bicyclo[3,3,0]-octan-3-one in 3 ml. of absolute DMSO is added dropwise to the red ylene solution, and the mixture is agitated for 2 hourt at 45°. The reaction mixture is poured on ice water, acidified to pH 4–5 with 10% citric acid solution, and extracted three times with methylene chloride. The organic phase is shaken with brine, dried over magnesium sulfate, and evaporated under vacuum. Chromatography of the residue on silica gel yields, with ether/pentane (3+2), 445 mg. of the olefin-formation product which, to split off the blocking groups, is stirred for 20 hours at 25° with 15 ml. of a mixture of acetic acid/water/tetrahydrofuran (65/35/10). The mixture is then evaporated under vacuum, and the residue is chromatographed on silica gel. With methylene chloride/isopropanol (95+5), the initial yield is 72 mg. of 5-{(E)-(1S,5S,6R,7R)-7-hydroxy-6-[(Z)-3α-hydroxyoct-1-en-6-inyl]bicyclo[3,3,0]octan-3-ylidene}-pentanoic acid and, as the more polar component, 121 mg. of the title compound as a colorless oil.

IR: 3600, 3420 (broad), 2945, 2860, 1712, 976 cm$^{-1}$.

The starting material for the above title compound is prepared as follows:

10(a)
(1R,5S,6R,7R)-3,3-Ethylenedioxy-7-benzoyloxy-6-[(E)-3-oxooct-1-en-6-inyl]bicyclo[3,3,0]octane Analogously to Example 1(a), 560 mg. of the aldehyde prepared according to Reference Example 1(q) and 0.5 g. of 2-oxohept-5-ynephosphonic acid dimethyl ester yield 0.62 g. of the title compound as a colorless oil.

IR: 2945, 2860, 1714, 1672, 1630, 1275, 978, 948 cm$^{-1}$.

10(b)
(1R,5S,6R,7R)-3,3-Ethylenedioxy-7-benzoyloxy-6-[(E)-3α-hydroxyoct-1-en-6-inyl]bicyclo[3,3,0]octan Analogously to Example 1(b), 400 mg. of the ketone prepared according to Example 10(a) and 220 mg. of sodium borohydride yield 135 mg. of the title compound as a colorless oil.

IR: 3600, 3410 (broad), 2940, 2860, 1715, 1603, 1590, 1278, 972, 948 cm$^{-1}$.

10(c)
(1R,5S,6R,7R)-3,3-Ethylenedioxy-7-hydroxy-6-[(E)-3α-hydroxyoct-1-en-6-inyl]bicyclo[3,3,0]octane Analogously to Example 1(c), 240 mg. of the α-alcohol prepared according to Example 10(b) and 165 mg. of potassium carbonate yield 230 mg. of the title compound as a colorless oil (crude product).

IR: 3600, 3440 (broad), 2945, 2860, 974, 948 cm$^{-1}$.

10(d)
(1R,5S,6R,7R)-7-Hydroxy-6-[(E)-3α-hydroxyoct-1-en-6-inyl]bicyclo[3,3,0]octan-3-one Analogously to Example 1(d), 230 mg. of the diol prepared according to Example 10(c) yields 141 mg. of the title compound as a colorless oil.

IR: 3640, 3610, 2945, 2865, 1740, 974 cm$^{-1}$.

10(e)
(1R,5S,6R,7R)-7-(Tetrahydropyran-2-yloxy)-6-[(E)-3α-(tetrahydropyran-2-yloxy)oct-1-en-6-inyl]bicyclo[3,3,0]octan-3-one In analogy to Example 1(e), 130 mg. of the ketone prepared according to Example 10(d) and 0.18 ml. of dihydropyran yield 230 mg. of the bis(tetrahydropyranyl)ether which is utilized for the Wittig reaction without further purification.

IR: 2960, 2860, 1740, 972 cm$^{-1}$.

EXAMPLE 11

5-{(E)-(1S,5S,6R,7R)-7-Hydroxy-6-[(E)-(4RS)-3α-hydroxy-4-methyloct-1-en-6-inyl]bicyclo[3,3,0]octan-3-ylidene}-pentanoic Acid At 15° under argon, 21.3 ml. of a 1.04-molar solution of methylsulfinylmethyl sodium in DMSO is added dropwise to a solution of 5.3 g. of 4-carboxybutyltriphenylphosphonium bromide in 12 ml. of absolute DMSO. The mixture is stirred for 30 minutes at room temperature. A solution of 870 mg. of (1R,5S,6R,7R)-7-(tetrahydropyran-2-yloxy)-6-[(E)-(4RS)-4-methyl-3α-(tetrahydropyran-2-yloxy)oct-1-en-6-inyl]bicyclo[3,3,0]octan-3-one in 6 ml. of absolute DMSO is added dropwise to the red ylene solution, and the mixture is stirred for 2 hours at 45°. The reaction mixture is poured on ice water, acidified to pH 5 with 10% citric acid solution, and extracted three times with methylene chloride. The organic phase is shaken with brine, dried over magnesium sulfate, and evaporated under vacuum. Chromatography of the residue on silica gel yields, with ether/pentane (3+2), 940 mg. of the olefin-formation product which, to split off the blocking groups, is agitated with 30 ml. of a mixture of acetic acid/water/tetrahydrofuran (65/35/10) for 20 hours at 25°. The mixture is evaporated under vacuum and the residue is chromatographed on silica gel. With methylene chloride/isopropanol (95+5), the yield is 165 mg. of 5-{(Z)-(1S,5S,6R,7R)-7-hydroxy-6-[(E)-(4RS)-3α-hydroxy-4-methyloct-1-en-6-inyl]bicyclo[3,3,0]octan-3-ylidene}-pentanoic acid, and as the more polar component 253 mg. of the title compound as a colorless oil.

IR: 3600, 3400 (broad), 2940, 2860, 1712, 975 cm$^{-1}$.

The starting material for the above title compound is prepared as follows:

11(a)
(1R,5S,6R,7R)-3,3-Ethylenedioxy-7-benzoyloxy-6-[(E)-(4RS)-4-methyl-3-oxooct-1-en-6-inyl]bicyclo[3,3,0]octane Analogously to Example 1(a), 1.3 g. of the aldehyde produced according to Reference Example 1(q) and 1 g. of 3-methyl-2-oxohept-5-ynephosphonic acid dimethyl ester yield 1.45 g. of the title compound as an oil.

IR: 2940, 2860, 1714, 1670, 1629, 1275, 978, 948 cm$^{-1}$.

11(b)
(1R,5S,6R,7R)-3,3-Ethylenedioxy-7-benzoyloxy-6-[(E)-(4RS)-3α-hydroxy-4-methyloct-1-en-6-inyl]bicyclo[3,3,0]octane Analogously to Example 1(b), 810 mg. of the ketone prepared according to Example 11(a) and 450 mg. of sodium borohydride yield 380 mg. of the title compound as a colorless oil.

IR: 3600, 3400 (broad), 2945, 2860, 1715, 1602, 1589, 1278, 973, 948 cm$^{-1}$.

11(c)
(1R,5S,6R,7R)-3,3-Ethylenedioxy-7-hydroxy-6-[(E)-(4RS)-3α-hydroxy-4-methyloct-1-en-6-inyl]bicyclo[3,3,0]octan-3-one In analogy to Example 1(c), 500 mg. of the α-alcohol obtained according to Example 11(b) and 340 mg. of potassium carbonate yield 465 mg. of the title compound as an oil (crude product).

IR: 3600, 3400 (broad), 2940, 2860, 976, 948 cm$^{-1}$.

11(d)
(1R,5S,6R,7R)-7-Hydroxy-6-[(E)-(4RS)-3α-hydroxy-4-methyloct-1-en-6-inyl]bicyclo[3,3,0]octan-3-one Analogously to Example 1(d), 455 mg. of the diol prepared according to Example 11(c) yields 295 mg. of the title compound as a colorless oil.

IR: 3600, 2945, 2860, 1740, 974 cm$^{-1}$.

11(e)
(1R,5S,6R,7R)-7-(Tetrahydropyran-2-yloxy)-6-[(E)-(4RS)-4-methyl-3α-(tetrahydropyran-2-yloxy)oct-1-en-6inyl]bicyclo[(3,3,0]octan-3-one In analogy to Example 1(e), 270 mg. of the ketone prepared according to Example 11(d) and 0.38 ml. of dihydropyran yield 460 mg. of the bis(tetrahydropyranyl)ether which is used for the Wittig reaction without further purification.

IR: 2960, 2865, 1738, 975 cm$^{-1}$.

EXAMPLE 12
5-{(E)-(1S,5S,6R,7R)-7-Hydroxy-6-[(E)-3α,β-hydroxy-3-methyloct-1-en-6-inyl]bicyclo[3,3,0]octan-3-ylidene}-pentanoic Acid At 15° under argon, 6 ml. of a 1.04 molar solution of methylsulfinylmethyl sodium in DMSO is added dropwise to a solution of 1.50 g. of 4-carboxybutyltriphenylphosphonium bromide in 5 ml. of absolute DMSO. After 15 minutes the mixture is combined with 250 mg. of (1S,5S,6R,7R)-7-(tetrahydropyran-2-yloxy)-6-[(E)-3α,β-methyl-3-(tetrahydropyran-2-yloxy)oct-1-en-6-inyl]bicyclo[3,3,0]octan-3-one, dissolved in 3ml. of absolute DMSO, and the mixture is stirred for 2 hours at 50°. After dilution with ice water and acidification with dilute citric acid solution to pH 4.5, the mixture is repeatedly extracted with methylene chloride, the extract is washed with brine, dried over magnesium sulfate, and evaporated under vacuum. After chromatography of the residue on silica gel, 270 mg. of a crude product is obtained with ether/pentane (1+1) which, for splitting off the blocking groups, is stirred for 20 hours at 25° with 8 ml. of a mixture of acetic acid/water/tetahydrofuran (65/35/10). The mixture is evaporated under vacuum, and the residue is chromatographed on silica gel with methylene chloride/1-5% isopropanol, thus obtaining initially 35 mg. of 5-{(Z)-(1S,5S,6R,7R)-7-hydroxy-6-[(E)-3α,β-hydroxy-3-methyloct-1-en-6-inyl]bicyclo[3,3,0]octan-3-ylidene}-pentanoic acid and, as the more polar component, 55 mg. of the title compound as a colorless oil.

IR: 3600, 3420 (broad) 2950, 2865, 1710, 978 cm$^{-1}$.

The starting material for the above title compound is produced as follows:

12(a)
(1R,5S,6R,7R)-3,3-Ethylenedioxy-7-benzoyloxy-6-[(E)-3α,β-hydroxy-3-methyloct-1-en-6-inyl]bicyclo[3,3,-0]octane At −60°, 30 ml. of an ether solution of methylmagnesium bromide solution (prepared from 0.1 mole of magnesium) is added dropwise to a solution of 4 g. of (1R,5S,6R,7R)-3,3-ethylenedioxy-7-benzoyloxy-6-[(E)-3-oxo-oct-1-en-6-inyl]bicyclo[3,3,0]octane [preparation see Example 10(a)] in 150 ml. of absolute tetrahydrofuran. The mixture is agitated for 15 minutes and then poured in 200 ml. of saturated ammonium chloride solution. The reaction mixture is agitated for 10 minutes at 20°, extracted four times with respectively 75 ml. of ether, the combined extracts are washed twice with repsectively 30 ml. of brine, dried over magnesium sulfate, and evaporated under vacuum. Purification by column chromatography on silica gel with hexane/ethyl acetate mixtures yields 3.5 g. of the above alcohol as an oil.

IR: 3600, 3450 (broad), 2960, 2865, 1715, 1602, 1588, 1275, 976, 948 cm$^{-1}$.

12(b):
(1R,5S,6R,7R)-3,3-Ethylenedioxy-7-hydroxy-6-[(E)-3α,β-hydroxy-3-methyloct-1-en-6-inyl]bicyclo[3,3,-0]octane A solution of 3.3 g. of the alcohol prepared according to Example 12(a) in 300 ml. of methanol is agitated for 16 hours at 25° with 2.5 g. of potassium carbonate. Then the methanol is evaporated under vacuum, the residue is distributed between methylene chloride and water, the organic phase is dried over magnesium sulfate and evaporated under vacuum. The residue is filtered over silica gel with hexane/ethyl acetate mixtures, thus obtaining 2.20 g. of the above diol as a colorless oil.

IR: 3600, 3450 (broad), 2965, 2870, 978, 948 cm$^{-1}$.

12(c)
(1R,5S,6R,7R)-7-Hydroxy-6-[(E)-3α,β-hydroxy-3-methyloct-1-en-6-inyl]bicyclo[3,3,0]octan-3-one 2 g of the diol prepared according to Example 12(b) is agitated for 20 hours with 50 ml. of a mixture of acetic acid/water/tetrahydrofuran (65/35/10). The mixture is evaporated under vacuum while adding toluene, the residue is taken up in methylene chloride and shaken in succession with sodium bicarbonate solution and brine, dried over magnesium sulfate, and evaporated under vacuum, thus obtaining 1.6 g. of the above ketone as an oil.

IR: 3600, 3450 (broad), 2965, 2860, 1738, 976 cm$^{-1}$.

12(d)
(1R,5S,6R,7R)-7-(Tetrahydropyran-2-yloxy)-6-[(E)-3α,β-methyl-3-(tetrahydropyran-2-yloxy)oct-1-en-6-inyl]-bicyclo[3,3,0]octan-3-one A mixture of 1 g. of the ketone prepared according to Example 12(c), 50 ml. of methylene chloride, 1.5 ml. of dihydropyran, and 10 mg. of p-toluenesulfonic acid is agitated for 30 minutes at 0°-5°. Then the mixture is diluted with methylene chloride, shaken with sodium bicarbonate solution and brine, dried over magnesium sulfate, and evaporated under vacuum. The residue is chromatographed on silica gel with hexane/ethyl acetate mixtures, thus obtaining 1.25 g. of the above bis(tetrahydropyranyl) ether as a colorless oil.

IR: 2960, 2865, 1738, 978 cm$^{-1}$.

EXAMPLE 13

5-{(E)-(1S,5S,6R,7R)-7-Hydroxy-6-[(E)-(4RS)-3α-hydroxy-4-methyloct-1-en-6-inyl]bicyclo[3,3,0]octan-3-ylidene}-pentanoic Acid Methyl Ester A solution of 100 mg. of 5-{(E)-(1S,5S,6R,7R)-7-hydroxy-6-[(E)-(4RS)-3α-hydroxy-4-methyloct-1-en-6-inyl]bicyclo[3,3,0]-octan-3-ylidene}-pentanoic acid (preparation see Example 11) in 5 ml. of methylene chloride is combined under agitation dropwise at 0° with an ethereal diazomethane solution until the mixture assumes a permanent yellow coloring. After evaporation of the solvent, the residue is purified by chromatography on silica gel with methylene chlorode/1% isopropanol, thus obtaining 90 mg. of the title compound as an oil.

IR: 3600, 2960, 2865, 1735, 978 cm$^{-1}$.

EXAMPLE 14

5-{(E)-(1S,5S,6R,7R)-7-Hydroxy-6-[(E)-(4RS)-3α-hydroxy-4-methyloct-1-en-6-inyl]bicyclo[3,3,0]octan-3-ylidene}-pentanoic Act Tris (hydroxymethyl)aminomethane Salt At 65°, a solution of 121 mg. of tris(hydroxymethyl)aminomethane in 0.4 ml. of water is added to a solution of 360 mg. of 5-{(E)-(1S,5S,6R,7R)-7-hydroxy-6-[(E)-(4RS)-3α-hydroxy-4-methyloct-1-en-6-inyl]bicyclo[3,3,0]octan-3-ylindene}-pentanoic acid (preparation see Example 11) in 60 ml. of acetonitrile. The mixture is allowed to cool under agitation; after 16 hours, the product is decanted from the solvent, and the residue is dried at 25° and under 0.1 torr, thus obtaining 320 mg. of the title compound as a waxy mass.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A prostane derivative of the formula

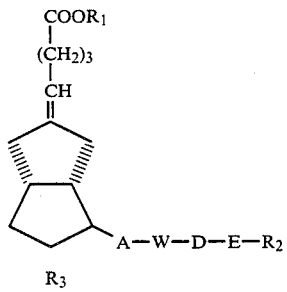

wherein
$R_1$ is (a) hydrogen, (b) $C_{1-10}$ alkyl, (c) $C_{1-10}$ alkyl substituted by halogen; $C_{1-4}$ alkoxy; $C_{6-10}$ aryl; $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group; di-$C_{1-4}$-alkylamino; or tri-$C_{1-4}$-alkylammonium; (d) $C_{4-10}$ cycloalkyl, (e) $C_{4-10}$ cycloalkyl substituted by $C_{1-4}$ alkyl, (f) $C_{6-10}$ aryl, (g) $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group, or (h) an aromatic heterocycle of 5 or 6 ring atoms one of which is O, N or S, the remainder being carbon atoms;

A is —CH$_2$—CH$_2$—, trans—CH=CH— or —C≡C—;

W is hydroxymethylene, RO-methylene,

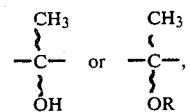

wherein OH or OR is in the α- and/or β-position and R is tetrahydropyranyl, tetrahydrofuranyl, α-ethoxyethyl, trimethylsilyl, dimethyl-tert-butylsilyl, tribenzylsilyl or an acyl group of a $C_{1-15}$-hydrocarbon carboxylic or sulfonic acid;

D is $C_{1-10}$ alkylene, $C_{2-10}$ alkenylene or $C_{2-10}$ alkynylene or one of these groups substituted by fluorine, and E is —C≡C—;

$R_2$ is (a) a $C_{1-10}$ hydrocarbon aliphatic radical, (b) a $C_{6-10}$ hydrocarbon aliphatic radical substituted by $C_{6-10}$ aryl or by $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group; (c) $C_{4-10}$ cycloalkyl, (d) $C_{4-10}$ cycloalkyl substituted by $C_{1-4}$ alkyl, (e) $C_{6-10}$ aryl, (f) $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group; or (h) an aromatic heterocycle of 5 or 6 ring atoms, one of which is O, N or S, the remainder being carbon atoms; and $R_3$ is OH or OR; or, when $R_1$ is hydrogen, a physiologically compatible salt thereof with a base.

2. A compound of claim 1 containing a 16-methyl group.

3. 5-{(E)-(1S,5S,6R,7R)-7-Hydroxy-6-[(E)-3α-hydroxy-oct-1-en-6-inyl]bicyclo[3,3,0]octan-3-ylidene}-pentanoic acid, a compound of claim 1.

4. 5-{(E)-(1S,5S,6R,7R)-7-Hydroxy-6-[(E)-(4RS)-3α-hydroxy-4-methyloct-1-en-6-inyl]bicyclo[3,3,0]-octan-3-ylidene}-pentanoic acid, a compound of claim 1.

5. 5{(E)-(1S,5S,6R,7R)-7-Hydroxy-6-[(E)-3α,β-hydroxy-3-methyloct-1-en-6-inyl]bicyclo[3,3,0]octan-3-ylidene}-pentanoic acid, a compound of claim 1.

6. 5-}(E)-(1S,5S,6R,7R)-7-Hydroxy-6-[(E)-(4RS)-3α-hydroxy-4-methyloct-1-en-6-inyl]bicyclo[3,3,0]octan-3-ylidene}-pentanoic acid methyl ester, a compound of claim 1.

7. 5-{(E)-(1S,5S,6R,7R)-7-Hydroxy-6-[(E)-(4RS)-3α-hydroxy-4-methyloct-1-en-6-inyl]bicyclo[3,3,0]octan-3-ylidene}-pentanoic acid tris(hydroxymethyl)aminomethane salt, a compound of claim 1.

8. A compound of claim 1, wherein $R_1$ is H.

9. A compound of claim 1, wherein W and $R_3$ are each OH.

10. A compound of claim 1, wherein $R_1$=H, $R_3$=OH, A=—trans—C=C—, W=—CHOH—, $R_2$=$C_{1-7}$-alkyl, E=—C≡C— and D=saturated-$C_{1-10}$-alkylene.

11. A compound of claim 10 wherein $R_2$=methyl, ethyl, propyl, butyl, isobutyl, t-butyl or pentyl.

12. A compound of claim 10, wherein $R_2$=methyl or ethyl.

13. A compound of claim 10, wherein D is straight chained alkylene.

14. A compound of claim 10, wherein D is ethylene.

15. A compound of claim 11, wherein D is ethylene.

16. A compound of claim 12, wherein D is ethylene.

17. A compound of claim 10, wherein D is 1,2-propylene or ethylethylene.

18. A compound of claim 10, wherein D is branched alkylene.

19. A compound of claim 12, wherein D is branched alkylene.

20. A compound of claim 1, wherein A is —CH$_2$—CH$_2$—.

21. A compound of claim 1, wherein A is —trans—CH=CH—.

22. A compound of claim 1 wherein A is —C=C—, D=saturated —C$_{1-10}$-alkylene, and E is —C≡C—.

23. A compound of claim 22 wherein D is ethylene.

24. A compound of claim 22 wherein R$_2$ is —C$_{1-7}$-alkyl.

25. A compound of claim 23 wherein R$_2$ is —C$_{1-7}$-alkyl.

26. A pharmaceutical composition comprising a thrombocyte aggregation inhibiting.

27. A pharmaceutical composition comprising a thrombocyte aggregation inhibiting effective amount of a compound of claim 4 and a pharmaceutically acceptable adjuvant.

28. A pharmaceutical composition comprising a thrombocyte aggregation inhibiting effective amount of a compound of claim 22 and a pharmaceutically acceptable adjuvant.

29. A method of inhibiting thrombocyte aggregation in a patient which comprises administering an effective amount of a compound of claim 1 to the patient.

30. A method of inhibiting thrombocyte aggregation in a patient in need of such treatment comprising administering to the patient an effective amount of a compound of claim 4.

31. A method of inhibiting thrombocyte aggregation in a patient in need of such treatment comprising administering to the patient an effective amount of a compound of claim 22.

* * * * *

UNITED STATES PATENT AND TRADEMARK OFFICE
CERTIFICATE OF CORRECTION

PATENT NO. : 4,692,464

DATED : September 8, 1987

INVENTOR(S) : Skuballa et al.

It is certified that error appears in the above-identified patent and that said Letters Patent is hereby corrected as shown below:

Column 31, formula for Claim 1:

Should Read: --
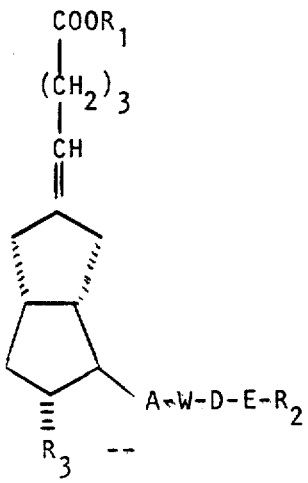
--

Column 32, Claim 10, Line 62:

Should Read: --$R_3$=OH. A=-trans-CH=CH-, W=-CHOH-, --

UNITED STATES PATENT AND TRADEMARK OFFICE
CERTIFICATE OF CORRECTION

PATENT NO. : 4,692,464

DATED : September 8, 1987

INVENTOR(S) : Skuballa et al.

It is certified that error appears in the above-identified patent and that said Letters Patent is hereby corrected as shown below:

Column 33, Claim 22, Line 16:

Should Read: -- A compound of claim 1, wherein A is trans-CH=CH-, --

Column 34, Claim 26, Line 2:

Should Read: -- thrombocyte aggregation inhibiting effective amount of a compound of claim 1 and a pharmaceutically acceptable carrier. --

Signed and Sealed this

Second Day of May, 1989

Attest:

DONALD J. QUIGG

Attesting Officer

Commissioner of Patents and Trademarks